(12) United States Patent
Jarrott

(10) Patent No.: US 8,716,528 B2
(45) Date of Patent: May 6, 2014

(54) ARYLOXY AMINE COMPOUNDS AND THEIR USE AS SODIUM CHANNEL MODULATORS

(75) Inventor: Bevyn Jarrott, North Melbourne (AU)

(73) Assignee: Howard Florey Institute (AU)

( * ) Notice: Subject to any disclaimer, the term of this patent is extended or adjusted under 35 U.S.C. 154(b) by 428 days.

(21) Appl. No.: 12/741,124

(22) PCT Filed: Oct. 31, 2008

(86) PCT No.: PCT/AU2008/001624
§ 371 (c)(1),
(2), (4) Date: Sep. 29, 2010

(87) PCT Pub. No.: WO2009/055869
PCT Pub. Date: May 7, 2009

(65) Prior Publication Data
US 2011/0021577 A1      Jan. 27, 2011

Related U.S. Application Data

(60) Provisional application No. 60/984,681, filed on Nov. 1, 2007.

(51) Int. Cl.
*C07C 213/00* (2006.01)
*C07C 215/00* (2006.01)
*C07C 217/00* (2006.01)

(52) U.S. Cl.
USPC ........................................................ 564/348

(58) Field of Classification Search
None
See application file for complete search history.

(56) References Cited

U.S. PATENT DOCUMENTS 6,420,354 B1    7/2002 Marquess et al.

FOREIGN PATENT DOCUMENTS

EP       543662 A2    5/1993

OTHER PUBLICATIONS

Ni et al. "Synthesis and anticonvulsant activity of mexiletine derivatives" Zhangguo Yaoke Daxue Xuebao, 1990, 21(6), 321-324.*
Ni, Peizhou et al. Zhongguo Yaoke Daxue Xuebao, 21(6), 1990, 321-324.*
International Search Report, Nov. 2008.

* cited by examiner

*Primary Examiner* — Clinton Brooks
(74) *Attorney, Agent, or Firm* — Banner & Witcoff, Ltd.

(57) ABSTRACT

The present invention relates generally to the field of therapeutic treatment and compounds having utility therefor, in particular the therapy or management of conditions associated with excessive, unwanted or undesirable sodium ion passage through cellular membranes via voltage-gated sodium channels. In one embodiment the invention is concerned with the treatment of neuropathic pain. The invention contemplates to aryloxy-substituted amines, as sodium channel blockers or modulators. In further embodiments, the invention also relates to compounds which may advantageously have dual sodium channel blocker/modulating and antioxidative (free-radical scavenging) effects. Methods for their manufacture and compositions containing the compounds are also contemplated.

8 Claims, 7 Drawing Sheets

ARYLOXY AMINE COMPOUNDS AND THEIR USE AS SODIUM CHANNEL MODULATORS

BACKGROUND OF THE INVENTION

1. Field of the Invention

The present invention relates generally to the field of therapeutic treatment and compounds having utility therefor, in particular the therapy or management of conditions associated with excessive, unwanted or undesirable sodium ion passage through cellular membranes via voltage-gated sodium channels. In one embodiment the invention is concerned with the treatment of neuropathic pain. The invention contemplates to aryloxy-substituted amines, as sodium channel blockers or modulators. In further embodiments, the invention also relates to compounds which may advantageously have dual sodium channel blocker/modulating and antioxidative (free-radical scavenging) effects. Methods for their manufacture and compositions containing the compounds are also contemplated.

2. Description of the Prior Art

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The electrical potential difference across a neuronal cell membrane is the result of an inequitable distribution of ions on either side of the membrane. In its resting state, a neuron has a high internal store of potassium ions ($K^+$) with sodium ions ($Na^+$) accumulated on the outside of the membrane. In such a state, the flow of ions across a membrane is such that their movement causes no net change in charge. However, a perturbation of this resting flow results in an alteration of the membrane's potential.

Sodium channels are aqueous pores in the cellular membrane which regulate and provide a selective passage for sodium ions between the internal and external environments of a cell. Voltage-gated sodium channels, ie. those opened by changes in membrane potential, are largely responsible for the depolarization of the cell. When closed, they help maintain the neuron's resting potential, and when open, allow sodium ions to flow down the electrochemical gradient and depolarize the cell.

The voltage-gated sodium channel is formed by proteins embedded within the cell's membrane and has three known subunits: a large glycoprotein called the α-subunit, which probably forms the channel's pore, and two smaller polypeptides called γ1 and β2 which regulate the function of the α-subunit. γ- and δ-Subunits may also exist to regulate the α-subunit.

The α-subunit has four repeats, labelled I through IV, of the same 150 amino acid sequence. Each repeat contains six membrane-spanning regions labelled S1 through S6. The highly conserved S4 region, thought to be part of the channel that acts as its voltage sensor, has a positive amino acid at every third position, with hydrophobic residues between these. It is thought that when stimulated by a change in transmembrane voltage, this subunit moves from within the pore toward the extracellular side of the cell, allowing the channel to become permeable to ions which would otherwise have been blocked by the subunit's positive charges.

Voltage-gated sodium channels can have three states: resting (closed), activated (open), and inactivated (closed). Channels in the resting state are blocked on their intracellular side by an "activation gate" which is removed in response to stimulation that opens the channel. The ability to inactivate is thought to be due to a tethered plug (formed by domains III and IV of the alpha subunit), called an inactivation gate, that blocks the inside of the channel shortly after it has been activated. During an action potential the channel remains inactivated for a few milliseconds after the neuron is finished depolarizing. The inactivation is removed when the membrane potential of the neuron becomes negative after the falling phase of the action potential. This allows the channels to be activated again during the next action potential.

The inner pore of sodium channels contains a selectivity filter made of negatively charged amino acid residues (aspartic acid and glutamic acid), which attract the positive $Na^+$ ion and keep out negatively charged ions such as chloride. The mouth of the pore is some 1.2 nm wide, narrowing to about 0.3 by 0.5 nm wide, which is just large enough to allow a single $Na^+$ ion with a water molecule associated to pass through whilst being small enough to exclude larger $K^+$ ions. Differently sized ions also cannot interact as well with the negatively charged glutamic acid residues that line the pore. Voltage-gated sodium channels are further characterised with regard to their voltage dependence and kinetic behaviour.

Opening of $Na^+$ channels in response to an electrical stimulus results in a rapid influx of sodium ions. This causes a small localised disturbance in the membrane potential which open voltage-gated $Na^+$ channels in adjacent areas of the membrane, where in turn, the membrane's electrical potential changes as ions flow across. After the excitatory stimulus, the $Na^+$ channels close and the membrane potential is restored to its resting value by an outflow of potassium ions.

Thus, changes in membrane potential are propagated along the membrane from the point of stimulation. A self-propagating wave of depolarization down the axon of a neuron is known as an action potential. The more $Na^+$ channels which exist in a neuron's membrane, the faster the action potential will propagate down the axon. When it reaches the end of the axon, the action potential may electrically stimulate the membrane of an adjacent cell or release neurotransmitters into the synaptic cleft, which chemically open gated channels in the adjacent cell membrane. Voltage-gated sodium channels thus play a prominent and significant role in action potentials and, ultimately, the electrical activity of the central and peripheral nervous systems.

Notwithstanding the essential role of voltage-gated sodium channels in the central and peripheral nervous systems, it is now well established that they also implicated in the aetiology of a number of neuronal diseases and conditions (neuropathies). Depending on the particular nerves involved, the neuropathy can be classified as a central or peripheral neuropathy. Central neuropathies arise from spinal cord, brainstem, thalamic, and cerebral damage or disease, while peripheral neuropathies arise from damage or disease of peripheral nerves.

The peripheral nervous system transmits information from the brain and spinal cord to every other part of the body. More than 100 types of peripheral neuropathy have been identified, each with its own characteristic set of symptoms, pattern of development, and prognosis. Impaired function and symptoms depend on the type of nerves—motor, sensory, or autonomic—that are damaged. Some people may experience temporary numbness, tingling, and pricking sensations, sensitivity to touch, or muscle weakness. Others may suffer more extreme symptoms, including burning pain (especially at night), muscle wasting, paralysis, or organ or gland dysfunction. Peripheral neuropathy may be either inherited or acquired. Causes of acquired peripheral neuropathy include systemic diseases (e.g. diabetes), physical injury (trauma) to a nerve, tumors, toxins, autoimmune responses, viral and bacterial infections, nutritional deficiencies, alcoholism, and vascular and metabolic disorders. Inherited forms of peripheral neuropathy are caused by genetic mutations.

Central neuropathy, as the name implies, is the result of damage to the central nervous system, i.e. brain and spinal cord. As with peripheral neuropathies, the causes are varied and include physical injury, disease and autoimmune responses.

A particular example of such a neuropathy is multiple sclerosis (MS) which is a chronic, often disabling, disease that randomly attacks the central nervous system. The progress, severity and specific symptoms of the disease cannot be predicted; symptoms may range from tingling and numbness to paralysis and blindness. MS is a devastating disease because people live with its unpredictable physical and emotional effects for the rest of their lives. Symptoms of MS are unpredictable and vary greatly from person to person and from time to time in the same person. They may include: fatigue, impaired vision, loss of balance and muscle coordination, slurred speech, tremors, stiffness, bladder and bowel problems, difficulty walking, short-term memory loss, mood swings and, in severe cases, partial or complete paralysis.

A significant contributor to non-remitting deficits in demyelinating neuroinflammatory diseases such as MS and the related Guillain-Barre's syndrome (GBS), and their respective animal models, experimental allergic encephalomyelitis (EAE) and experimental autoimmune neuritis (EAN), is axonal loss. Recent studies have demonstrated that persistently activated sodium channels can trigger axonal injury by providing a sustained sodium influx that can drive reverse sodium-calcium exchange (Stys et al., 1992b, 1993; Craner et al., 2004) and sodium channel blockade can prevent axonal degeneration within white matter tracts in a variety of disease models (Stys et al., 1992a,b; Rosenberg et al., 1999; Kapoor et al., 2003; Lo et al., 2003; Bechtold et al., 2004). In addition, it has recently been demonstrated that the sodium channel blocker phenyloin inhibits immune cells in the neuroinflammatory disorders (Craner et al., 2005), and that administration of the sodium channel blocker flecainide in the EAN model, significantly increased the number of functional axons and significantly decreased axonal loss (Bechtold et al., 2005).

Physical trauma (car accident, gunshot, falls, etc.) or disease (polio, spina bifida, Friedreich's Ataxia, etc.) can lead to spinal cord injury (SCI)— damage to the spinal cord that results in a loss of function such as mobility or feeling. The spinal cord does not have to be severed in order for a loss of functioning to occur. In fact, in most people with SCI, the spinal cord is intact, but the damage to it results in loss of functioning. The extent of loss of function will vary depending on the area of injury but can range from quadriplegia, partial loss of function or dexterity in the arms and hands, paraplegia, poor trunk control as the result of lack of abdominal muscle control reduced control of the hip flexors and legs. Besides a loss of sensation or motor functioning, individuals with SCI also experience other changes. For example, they may experience dysfunction of the bowel and bladder. Very high injuries (C-1, C-2) can result in a loss of many involuntary functions including the ability to breathe, necessitating breathing aids such as mechanical ventilators or diaphragmatic pacemakers. Other effects of SCI may include low blood pressure, inability to regulate blood pressure effectively, reduced control of body temperature, inability to sweat below the level of injury, and chronic pain.

Secondary cell injury due to spinal cord trauma results, in part, from the accumulation of calcium ions within injured neurons and their axons. As noted above, this arises due to reverse operation of the sodium-calcium exchanger, which in turn is triggered by an increase in intracellular sodium concentration via persistently activated voltage-gated sodium channels. Pharmacological blockade of sodium channels has been shown to prevent axonal degeneration and preserve function after injury to central nervous system white matter tracts. Sodium channel blockade with tetrodotoxin (TTX), and tertiary and quaternary amine local anaesthetics have been shown to prevent the development of irreversible dysfunction of axons within the anoxic optic nerve (Stys et al., 1992a,b) and spinal cord (Imaizumi et al., 1997) in vitro. TTX applied focally after contusion spinal cord injury (SCI) reduces axoplasmic pathology and damage to myelin, results in residual white matter sparing, and enhances behavioral recovery (Rosenberg et al., 1999; Teng and Wrathall, 1997). Systemic lidocaine after compression SCI results in improved recovery of somatosensory-evoked responses (Kobrine et al., 1984). A charged derivative of lidocaine, QX-314, given after compression SCI partially preserves descending motor axons (Agrawal and Fehlings, 1997). In vitro studies have demonstrated that phenyloin, a drug that blocks sodium channels and inhibits persistent sodium currents (Chao and Alzheimer, 1995; Segal and Douglas, 1997), has a protective effect on axons within white matter after anoxia (Fern et al., 1993). Phenyloin given after compression SCI results in less tissue loss at the injury epicenter, but in these animals, measures of motor function were reported to be poorer (Schwartz and Fehlings, 2001). Phenyloin has recently been shown to protect against axonal degeneration of spinal cord axons and improve neurological outcome in mice with experimental allergic encephalomyelitis (Lo et al., 2002, 2003). The sodium channel blocker flecainide has a similar protective effect (Bechtold et al., 2004). It was subsequently shown that treatment with phenytoin after SCI confers substantial neuroprotection, with sparing of both white and grey matter surrounding the impact site, exerts a protective effect on axons, reduces loss of action potential conduction along spinal cord axons through the impact site and promotes locomotor recovery (Hams et al., 2004).

Many peripheral or central neuropathic conditions commonly result in pain. Pain can be classed as acute (or nociceptive) or neuropathic.

Nociceptive pain is mediated by thermal, mechanical, electrical or chemical stimulation of pain receptors, known as nociceptors, which are located in skin, bone, connective tissue, muscle and viscera. Its purpose is to serve as a protective biological warning of potential ongoing tissue damage and is experienced in and around the point of injury. It usually responds to opioid and/or Non Steroidal Anti-Inflammatory (NSAID) treatment. In the main, as healing progresses, the pain and inflammation associated with an injury abates and resolves.

In contrast, individuals may experience pain in the absence of an obvious tissue injury, or suffer chronic or protracted pain long after the injured tissue is apparently healed. Such pain serves no protective biological function and is predominantly neuropathic in nature, thus referred to as neuropathic pain. Neuropathic pain has been variously described as pain that results from a pathologic change in nerves or pain initiated or caused by a primary lesion or dysfunction in the nervous system (Mersky and Bogduk, 1994; De Andres and Garcia-Ribas, 2003) and can be described as burning, electric, tingling and shooting in nature. Neuropathic pain is associated with a variety of disease states and presents in the clinic with a wide range of symptoms. (Woolf and Mannion, 1999). The damage to the nerves may be caused by accidental or surgical injury, by metabolic disturbances such as diabetes or vitamin B12 or other nutrient deficiency, by ischaemia, by radiation, by autoimmune attack, by cytotoxic drugs used in cancer chemotherapy, by alcohol, by infections, especially viral infections, particularly with the herpes virus, by tumours, by degenerative diseases, or by unknown factors such as may be operative in trigeminal and other neuralgias. Neuropathic pain does not require specific pain receptor stimulation although such stimulation can add to the intensity of the pain sensation (Baron, 2003).

Neuropathic pain is often characterised by chronic allodynia and/or hyperalgesia. Allodynia is pain resulting from a non-noxious stimulus, ie a stimulus that does not ordinarily cause a painful response, eg a light touch. Hyperalgesia, on the other hand, is an increased sensitivity to noxious stimuli (injury), ie a greater than normal pain response, and can be further defined as primary, occurring immediately in the vicinity of an injury, or secondary, occurring in undamaged area remote from an injury. Neuropathic pain is usually unresponsive to treatments used for nociceptive pain.

It is estimated that neuropathic pain affects over 26 million people worldwide (Butera 2007) and despite its common occurrence, neuropathic pain remains one of the most poorly understood and untreated conditions in primary care and can have a debilitating effect on almost all aspects of a sufferer's life. It has been associated with depression, anxiety, loss of independence and can impact on an individual's relationships and ability to work. The annual cost of neuropathic pain in the United States alone, including medical expenses, lost income and lost productivity is estimated to be $100 billion. The condition is particularly prevalent amongst the elderly and is experienced by a significant proportion of patients suffering from other disease states such as diabetes and advanced cancer.

Sodium channel blockers have been reported as useful agents in the treatment of neuropathic pain (Tanelian et al, 1995; Kyle and Ilyin, 2007). There is evidence that sodium channel blockers selectively suppress etopic neural firing in injured (unmyelinated) nerves, which have an accumulation of sodium channels, and studies carried out on known blockers, such as carbamazepine, phenyloin, lidocaine and mexiletine, have demonstrated utility in the treatment of various types of neuropathic pain. Consistent with this, is the demonstration that sodium channels accumulate in the peripheral nerve sites of axonal injury (Devor et al, 1993) and also in second order sensory neurons in pain pathways in the spinal cord (Hams et al, 2004 b). Alterations in the either the level of expression or distribution of sodium channels within an injured nerve, therefore, have a major influence on the pathophysiology of pain associated with this type of trauma.

Given the individual and social impact of the central and peripheral nervous system disease states, including neuropathic pain, and conditions in which excessive, undesirable or otherwise unwanted sodium channel activity is involved or implicated, there remains the need for new compounds, which may act as sodium channel inhibitors or modulators to ameliorate, relieve, prevent or otherwise improve one or more of their symptoms, or the conditions themselves.

SUMMARY OF THE INVENTION

It has now been found that certain aryloxy amine compounds, specifically bearing a disubstituted phenol moiety, exhibit sodium channel blocking or modulating activity. In certain embodiments, this activity is substantially improved in comparison to a known aryloxy amine compound without the disubstituted phenol group (mexiletine), or compared to an aryloxy amine compounds which bears a different antioxdative group.

Accordingly, in a first aspect, the present invention provides a compound of Formula (I):

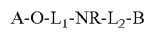

wherein

A is an optionally substituted cyclopentadi-2,4-en-1-yl or phenyl group, an optionally substituted 5-6-membered monocyclic heteroaryl group, an optionally substituted napthyl group or an optionally substuted 9-10-membered bicyclic heteroaryl group;

$L_1$ is an optionally substituted $C_{1-4}$ alkylene group, an optionally substituted $C_{2-4}$ alkenylene group or an optionally substituted $C_2$-$C_4$ alkynylene group;

$L_2$ is an optionally substituted $C_{1-4}$ alkylene group, an optionally substituted $C_{2-4}$ alkenylene group or an optionally substituted $C_2$-$C_4$ alkynylene group or a $CO_2$ group;

R is hydrogen or a $C_{1-6}$alkyl group; and

B is a group of formula (a) below:

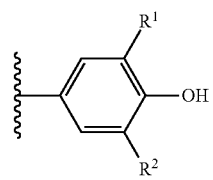

(a)

wherein $R^1$ and $R^2$ are independently selected from hydrogen, $C_{1-6}$ alkyl and $C_{3-6}$cycloalkyl;

or a pharmaceutically acceptable salt thereof.

In certain embodiments of the invention, $R^1$ and $R^2$ are not both hydrogen. Thus, in some embodiments, $R^1$ and $R^2$ are independently selected from $C_{1-6}$alkyl and $C_{3-6}$cycloalkyl. In other embodiments, one of $R^1$ and $R^2$ is hydrogen and the other is $C_{1-6}$alkyl or $C_{3-6}$cycloalkyl.

In another aspect, the invention provides a composition comprising a compound of Formula (I) or a pharmaceutically acceptable salt or solvate thereof together with a pharmaceutically acceptable additive.

Yet another aspect of the invention relates to a method for preventing sodium ion influx into a cell by blocking or modulating a sodium channel, said method comprising contacting said sodium channel with a compound of Formula (I) or a pharmaceutically acceptable salt thereof.

Another aspect of the invention relates to a method for treating a condition in which excessive or undesirable sodium channel activity is implicated, in a subject in need thereof, comprising administering to said subject a compound of Formula (I) or a pharmaceutically acceptable salt or solvate thereof.

Thus, one embodiment of the invention provides a method for treating a neuroinflammatory disease to a subject in need thereof comprising administering to said subject a compound of Formula (I) or a pharmaceutically acceptable salt or solvate thereof.

A further embodiment of the invention provides a method for treating neuropathic pain in a subject in need thereof, comprising administering to said subject, a compound of Formula (I) or a pharmaceutically acceptable salt thereof.

Yet another aspect provides a method for the treatment of spinal cord injury in a subject in need thereof, comprising administering to said subject, a compound of Formula (I) or a pharmaceutically acceptable salt thereof.

A still further aspect of the invention provides a method for treating axonal loss, degeneration or damage in a subject in need thereof, comprising administering to said subject, a compound of Formula (I) or a pharmaceutically acceptable salt thereof.

Yet another aspect of the invention relates to a method for treating a demyelinating disease in a subject in need thereof, comprising administering to said subject, a compound of Formula (I) or a pharmaceutically acceptable salt thereof.

Yet another aspect of the invention relates to a method for treating a central or peripheral neuropathy in a subject in need thereof, comprising administering to said subject, a compound of Formula (I) or a pharmaceutically acceptable salt thereof.

Where appropriate, $L_1$ and $L_2$ are independently substituted or unsubstituted and may be the same or different. $L_1$ and $L_2$ may be the same or different and are selected from substituted $C_{1-4}$alkylene and unsubstituted $C_{1-4}$alkylene.

In certain embodiments of the invention, A is an optionally substituted phenyl or 6-membered heteroaryl group. In other embodiments of the invention A is an optionally substituted cyclopentadi-2,4-en-1-yl or 5-membered heteroaryl group.

In some embodiments of the invention, $R^1$ and $R^2$ are independently straight, branched or cyclo-$C_{3-6}$alkyl. In further examples thereof, $R^1$ and $R^2$ are branched or cycloalkyl. In yet further examples, $R^1$ and $R^2$ are the same. In one particular example, $R^1$ and $R^2$ are both t-butyl. In another example, $R^1$ is hydrogen and $R^2$ is branched or cyclo-$C_{3-6}$alkyl, such as t-butyl.

DETAILED DESCRIPTION OF THE INVENTION

Figure 1:
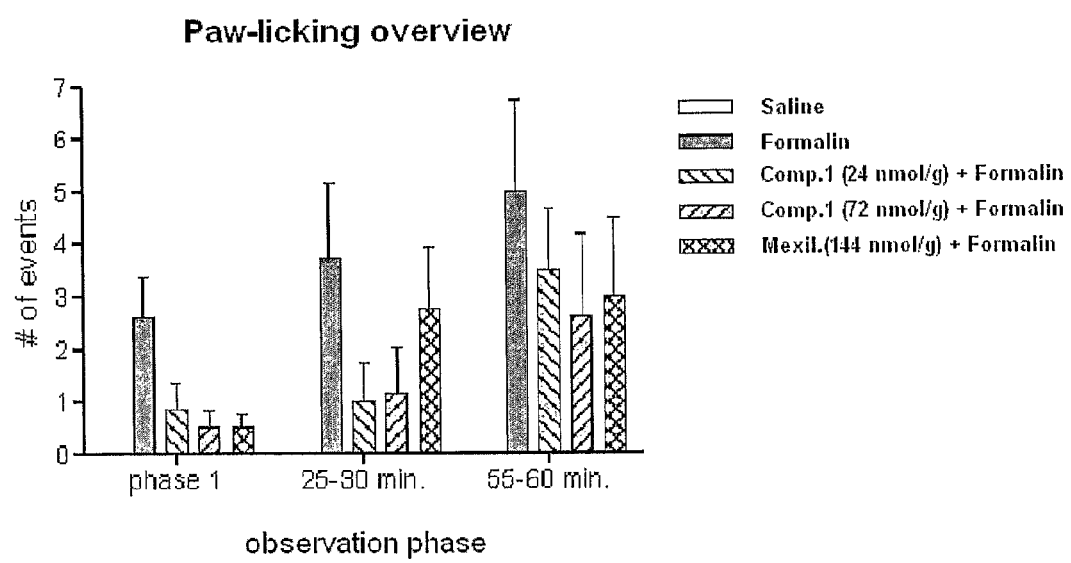
FIG. 1 graphically depicts the number of paw-licking events in a rat formalin paw model.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

The singular forms "a", "an" and "the" include plural aspects unless the context clearly dictates otherwise.

As used herein, the term "alkyl" or "alk", used either alone or in compound words denotes straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", butyl" etc, it will be understood that this can refer to any of straight or branched isomers where appropriate. An alkyl group may be optionally substituted by one or more optional substituents as herein defined.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl. An alkenyl group may be optionally substituted by one or more optional substituents as herein defined.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

An "alkylene", "alkenylene" or "alkynylene" group denotes a divalent form of an alkyl, alkenyl or alkynyl group and may be substituted or unsubstituted. Thus, "$C_{1-4}$alkylene" refers to straight or, where appropriate, branched, methylene, ethylene, propylene and butylene. "$C_{1-4}$Alkylene" refers to ethenylene, propenylene and butenylene, which may be straight, or as appropriate, branched. "$C_{1-4}$Alkynylene" refers to ethynylene, propynylene and butynylene, which may be straight, or as appropriate, branched.

The term "halogen" ("halo") denotes fluorine, chlorine, bromine or iodine (fluoro, chloro, bromo or iodo).

The term "heteroaryl" includes any of monocyclic or bicyclic, hydrocarbon residues, wherein one or more carbon atoms are replaced by a heteroatom so as to provide an aromatic residue. Monocyclic 5-6-membered heteroaryl refers to a single heteroaryl ring having 5-6 ring members. Bicyclic 9-10-membered heteroaryl refers to bicyclic heteroaryl ring systems, which may be fused, having a total of 9-10 ring members. Suitable heteroatoms include, O, N, S, P and Se, particularly O, N and S. Where two or more carbon atoms are replaced, this may be by two or more of the same heteroatom or by different heteroatoms. In particular embodiments of the invention, when A is a heteroaryl group, it is attached to the adjacent oxygen atom via a carbon atom. A heteroaryl group may be optionally substituted by one or more optional substituents as defined herein.

Suitable examples of monocyclic 5-6-membered heteroaryl groups may include pyrrolyl (2- or 3-), furanyl (2- or 3-), thienyl (2- or 3-), pyrazolyl (3-, 4-, or 5-), imidazolyl (4-, or 5-), oxazolyl (2-, 4-, or 5-), isoxazolyl (3-, 4- or 5-), thiazolyl (4-), isothiazolyl, 1,2,3-triazolyl, 1,2,4-triazolyl, 1,2,3-oxadiazolyl, oxatriazolyl, furazanyl, 1,3,4-thiadiazolyl, tetrazolyl, pyridyl, pyrazinyl, pyrimidinyl, pyridazinyl, and triazinyl, (1,2,3-, 1,3,5- or 1,2,4-). A 5-6-membered heteroaryl group may be attached via any ring carbon atom thereof, ie at positions 1-, 2-, 3-, 4-, 5- or 6- as appropriate. Some non-limiting exemplary positions are indicated in parentheses above.

Suitable examples of bicyclic 9-10 membered heteroaryl groups may include indolyl, isoinolyl, benzothienyl, isobenzothienyl, benzofuranyl, isobenzofuranyl, quinazolinyl, cinnolinyl, quinolyl, isoquinolyl, quinolinyl, isoquinolinyl, indazolyl, benzimidazolyl, benzthiazolyl, purinyl, quinoxalinyl, 1,8-napthpyridinyl, phthalazinyl, pteridinyl. Bicyclic groups, including naphthyl, are, in certain embodiments, attached such that the molecule is essentially linear, at a 2- or 3-(or corresponding) position.

In certain embodiments of the invention, A is optionally substituted phenyl or an optionally substituted 6-membered heteroaryl group, such as optionally substituted pyridyl (e.g. optionally substituted 4-pyridyl).

In some further examples, A is substituted with one, two or three substituents. In further examples, A is substituted at one or both of the positions ortho- to the atom bonded to the —O— atom.

In certain embodiments of the invention, $L_1$ and $L_2$ are independently selected from methylene, ethylene, propylene and butylene. Each linker group, $L_1$ and $L_2$, may be unsubstituted or independently substituted by one or more, same or different, substituents. Suitable substituents for $L_1$ and $L_2$ include $C_{1-6}$alkyl, such as methyl, ethyl and propyl (n- or i-). In certain examples, $L_1$ is unsubstituted. In further examples $L_1$ is unsubstituted ethylene or propylene, particularly unsubstituted propylene, and $L_2$ is unsubstituted methylene.

In some embodiments, R is hydrogen. In other embodiments, R is an alkyl group such as methyl, ethyl, or propyl (n- or i-).

In some embodiments of the invention, $R_1$ and $R_2$ are selected from $C_{3-6}$alkyl, which may be straight chain or branched, such as isopropyl, sec-butyl or t-butyl, or $C_{3-6}$cycloalkyl, for example, cyclopropyl or cyclobutyl. In particular embodiments of the invention, $R_1$ and $R_2$ are both t-butyl.

Certain groups as defined herein, for example the group A, may be optionally substituted, i.e., they may be unsubstituted or substituted by one or more, same or different substituents. Exemplary optional substituents include those selected from: alkyl, (e.g. $C_{1-6}$alkyl such as methyl, ethyl, propyl, butyl), cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl), alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl), alkoxy (e.g. $C_{1-6}$alkoxy, such as methoxy, ethoxy, propoxy, butoxy), alkoxyalkoxy (e.g. $C_{1-6}$alkocy$C_{1-6}$ alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy)cycloalkoxy (e.g. cyclopropoxy, cyclobutoxy, cyclopentoxyl, cyclohexyloxy), halo, haloalkyl(e.g. halo$C_{1-6}$ alkyl, such as chloromethyl, difluoromethyl, trifluoromethyl, trichloromethyl, tribromomethyl), haloalkoxy (e.g. halo$C_{1-6}$ alkoxy), hydroxy, thio (—SH), sulfonyl, sulfonamido, phenyl (which itself may be further substituted e.g., by one or more $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$ alkyl, NH$_2$, NHC$_{1-6}$ alkyl, NHC(O)$C_{1-6}$alkyl and NC$_{1-6}$ alkylC$_{1-6}$alkyl), benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$ alkyl, NH$_2$, NHC$_{1-6}$alkyl, NHC(O)$C_{1-6}$alkyl and NC$_{1-6}$ alkylC$_{1-6}$alkyl), phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$ alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, NH$_2$, NHC$_{1-6}$ alkyl, NHC(O) $C_{1-6}$alkyl and NC$_{1-6}$alkylC$_{1-6}$alkyl), benzyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$ alkyl, NH$_2$, NHC$_{1-6}$ alkyl, NHC(O)$C_{1-6}$alkyl and NC$_{1-6}$ alkylC$_{1-6}$alkyl), NH$_2$, alkylamino (e.g. —NHC$_{1-6}$alkyl, such as methylamino, ethylamino, propylamino etc), dialkylamino (e.g. —NH(C$_{1-6}$ alkyl)$_2$, such as dimethylamino, diethylamino, dipropylamino), acylamino (e.g. —NHC(O)$C_{1-6}$ alkyl, such as —NHC(O)CH$_3$), phenylamino (i.e. —NHphenyl, wherein phenyl itself may be further substituted e.g., by one or more of $C_{1-6}$alkyl, halo, hydroxy, hydroxy$C_{1-6}$alkyl, hydroxy$C_{1-6}$ alkoxy $C_{1-6}$alkoxy, $C_{1-6}$alkoxy$C_{1-6}$alkyl, $C_{1-6}$alkoxy$C_{1-6}$ alkoxy, halo$C_{1-6}$alkoxy, cyano, nitro, OC(O)$C_{1-6}$alkyl, NH$_2$, NHC$_{1-6}$alkyl, NHC(O)$C_{1-6}$alkyl and NC$_{1-6}$ alkylC$_{1-6}$alkyl), nitro, cyano, formyl, —C(O)-alkyl (e.g. —C(O)$C_{1-6}$alkyl, such as acetyl), O—C(O)-alkyl (e.g. —OC(O)$C_{1-6}$alkyl, such as acetyloxy), benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, NH$_2$, NHC$_{1-6}$ alkyl, NHC(O) $C_{1-6}$alkyl and NC$_{1-6}$alkylC$_{1-6}$alkyl), benzoyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, NH$_2$, NHC$_{1-6}$ alkyl, NHC(O)$C_{1-6}$alkyl and NC$_{1-6}$alkylC$_{1-6}$alkyl), CO$_2$H, CO$_2$alkyl (e.g. CO$_2$C$_{1-6}$alkyl such as methyl ester, ethyl ester, propyl ester, butyl ester), CO$_2$-phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$ alkyl, $C_{1-6}$alkoxy$C_{1-6}$alkoxy, halo$C_{1-6}$alkyl, halo$C_{1-6}$ alkoxy, cyano, nitro, OC(O)$C_{1-6}$alkyl, NH$_2$, NHC$_{1-6}$ alkyl, NHC(O)$C_{1-6}$alkyl and NC$_{1-6}$alkylC$_{1-6}$alkyl), CO$_2$-benzyl (wherein benzyl itself may be further substituted e.g., by one or more of $C_{1-6}$alkyl, halo, hydroxy, hydroxy$C_{1-6}$ alkyl, $C_{1-6}$alkoxy, $C_{1-6}$alkoxy$C_{1-6}$alkyl, $C_{1-6}$alkoxy$C_{1-6}$ alkoxy, halo$C_{1-6}$alkyl, halo$C_{1-6}$alkoxy, cyano, nitro, OC(O) $C_{1-6}$alkyl, NH$_2$, NHC$_{1-6}$alkyl, NHC(O)$C_{1-6}$alkyl and NC$_{1-6}$ alkylC$_{1-6}$alkyl), CONH$_2$, C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, NH$_2$, NHC$_{1-6}$ alkyl, NHC(O)C$_{1-6}$alkyl and NC$_{1-6}$alkylC$_{1-6}$alkyl), C(O)N-Hbenzyl (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), C(O)NHalkyl (e.g. C(O)NHC$_{1-6}$ alkyl such as methyl amide, ethyl amide, propyl amide, butyl amide) C(O)Ndialkyl (e.g. C(O)N(C$_{1-6}$alkyl)$_2$) aminoalkyl (e.g., HNC$_{1-6}$alkyl-, C$_{1-6}$alkylHN—C$_{1-6}$alkyl- and (C$_{1-6}$alkyl)$_2$N—C$_{1-6}$alkyl-), thioalkyl (e.g., HSC$_{1-6}$alkyl-), carboxyalkyl (e.g., HO$_2$CC$_{1-6}$alkyl-), carboxyesteralkyl (e.g., C$_{1-6}$alkylO$_2$CC$_{1-6}$alkyl-), amidoalkyl (e.g., H$_2$N(O)CC$_{1-6}$alkyl-, H(C$_{1-6}$alkyl)N(O)CC$_{1-6}$alkyl-), formylalkyl (e.g., OHCC$_{1-6}$alkyl-), acylalkyl (e.g., C$_{1-6}$alkyl(O)CC$_{1-6}$alkyl-), nitroalkyl (e.g., O$_2$NC$_{1-6}$alkyl-), replacement of CH$_2$ with C=O, replacement of CH$_2$ with C=S, substitution of 2 adjacent or non-adjacent carbon atoms (e.g. 1, 2 or 1,3) by one end each of a —O—(CH$_2$)$_s$—O— or —NR'—(CH$_2$)$_s$—NR'— group, wherein s is 1 or 2 and each R' is independently H or C$_{1-6}$alkyl, and substitution of 2 adjacent or non-adjacent atoms, independently selected from C and N, by a C$_{2-5}$alkylene or C$_{2-5}$alkenylene group.

The compounds of the invention may be prepared in accordance with the methods described herein or any other methods known in the art of synthetic organic chemistry.

In some embodiments, compounds of the invention may be prepared by reacting an appropriate aryloxyamine A-O-L$_1$-NH$_2$, (or suitable salt, for example as the hydrochloride salt thereof) with a disubstituted phenolic aldehyde in the presence of a base (eg an amine base such as Et$_3$N). Some exemplary aryloxyamine compounds, and their preparation, for use in accordance with this method are described in U.S. Pat. No. 3,659,019. Alternatively, aryloxyamine compounds can be prepared by reacting an appropriate A-OH compound with a suitable phthalimide compound in accordance or analogous to the preparative processes described in the Examples.

It will be recognised that during the processes for the preparation of compounds contemplated by the present invention, it may be necessary or desirable to protect certain functional groups which may be reactive or sensitive to the reaction or transformation conditions undertaken (e.g. OH (including diols), NH$_2$, CO$_2$H, SH, C=O). Suitable protecting groups for such functional groups are known in the art and may be used in accordance with standard practice. As used herein, the term "protecting group", refers to an introduced functionality which temporarily renders a particular functional group inactive under certain conditions. Such protecting groups and methods for their installation and subsequent removal at an appropriate stage are described in *Protective Groups in Organic Chemistry*, 3$^{rd}$ Edition, T. W. Greene and P. G. Wutz, John Wiley and Sons, 1999, the entire contents of which are incorporated herein by reference. Exemplary forms of protected groups include:

for amino (NH$_2$)—carbamates (such as Cbz, Boc, Fmoc), benzylamines, acetamides (e.g. acetamide, trifluoroacetamide);

for carbonyl—acetals, ketals, dioxanes, dithianes, and hydrazones;

for hydroxy—ethers (e.g. alkyl ethers, alkoxylalkyl ethers, allyl ethers, silyl ethers, benzyl ethers, tetrahydropyranyl ethers), carboxylic acid esters, acetals (e.g. acetonide and benzylidene acetal);

for thio (SH)—ethers (e.g. alkyl ethers, benzyl ethers), esters for CO$_2$H—esters (e.g. alkyl esters, benzyl esters).

It will also be recognised that certain compounds of formula (I) may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates, enzymes, or mixtures may be resolved by conventional methods, e.g., chromatography, recrystallization or use of a resolving agent.

The compounds of the present invention may also be administered as prodrugs and thus the invention also contemplates prodrugs of formula (I). The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters C$_{1-6}$alkyl esters; C$_{1-6}$alkoxymethyl esters, for example methoxymethyl or ethoxymethyl; C$_{1-6}$alkanoyloxymethyl esters, for example, pivaloyloxymethyl; phthalidyl esters; C$_{3-8}$cycloalkoxycarbonylC$_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and C$_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci,* 1983, 72, 1294, Johansen, M. et al), Mannich bases (see, for example, *J. Pharm. Sci.* 1980, 69, 44, Bundgaard, H. et al and *J. Am. Chem. Soc.,* 1959, 81, 1198, Gottstein, W. et al), hydroxymethyl derivatives (see, for example, *J. Pharm. Sci,* 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No. 5,684,018 and *J. Med. Chem.*, 1988, 31, 318-322, Alexander, J. et al). Esters of phosphoric acids such as phosphate esters of the phenolic hydroxy are also contemplated (see, for example, Mantyla et al, *J. Med. Chem.,* 47:188-195, 2004). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology,* 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews,* 8; 1-38 (1992); *Journal of Pharmaceutical Sciences,* 77; 285 (1988), H. Bundgaard, et al; *Chem Pharm Bull,* 32692 (1984), N. Kakeya et al and *The Organic Chemistry of Drug Desig and Drug Action*, Chapter 8, pp 352-401, Academic press, Inc., 1992.

Suitable pharmaceutically acceptable salts of compounds of formula (I) include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl) benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

The compounds of the invention may be in crystalline form either as the free compounds or as solvates and it is intended that both forms are within the scope of the present invention. The term "solvate" refers to a complex or aggregate formed by one or more molecules of a solute, ie compounds contemplated by the invention, and one or more molecules of a solvent. Suitable solvents are well understood in the art and include for example, of water, ie to form hydrates, and common organic solvents such as alcohols (methanol, ethanol, isopropanol) and acetic acid. Methods of solvation are generally known within the art, for example, recrystallization from an appropriate solvent.

Due to their sodium channel modulating properties, the compounds of the invention may be useful in the treatment of conditions in which excessive or undesirable sodium channel activity is implicated. Such conditions are those whose aetiologies or resulting symptoms have an excessive or undesirable sodium channel activity component, and include conditions such as arrhythmia and neuropathies, which may be central or peripheral as previously described herein above.

Central nervous system injuries (or neuropathies) which may be treated by compounds contemplated herein include those resulting from stroke, ischemic damage, percussive brain damage, traumatic damage, spinal cord injury, multiple sclerosis, Guillain-Barre syndrome, acute motor axonal neuropathy, acute inflammatory demyelinating polyneuropathy, Fisher syndrome, HIV infection or AIDS, and bacterial and viral infections eg meningitis and shingles (Herpes zoster infection).

The compounds contemplated herein may also be useful in the treatment of peripheral neuropathies which result in one or more of pain, tingling, numbness, cramps, itching, weakness, heaviness, muscular atrophy, fasciculation, and gait abnormalities. Peripheral neuropathies may be categorised as one of distal axonopathies (metabolic or toxic derangement of neurons), myelinopathies (primary attack on myelin causing an acute failure of impulse conduction) and neuronopathies (result of destruction of peripheral nervous system neurons) and may affect just one nerve (mononeuropathy) or several nerves (polyneuropathy). Peripheral neuropathies may be the result of compression or entrapment (such, as ulnar nerve palsey, carpal tunnel syndrome, peroneal nerve palsy and radial nerve palsey) metabolic diseases (such as diabetes or amyloidosis), renal failure, deficiency syndromes such as malnutrition and alcoholism, infectious disorders (eg, Lyme disease, HIV infection, leprosy), the effects of toxins or cytotoxic drugs, Sjögren's syndrome and Guillain-Barre syndrome.

In certain embodiments, compounds of the invention may be useful in the treatment of neuropathic pain. Neuropathic pain may result from peripheral or central nervous system disorders as described above, including pathologic events, ongoing metabolic or toxic diseases, infections, or endocrinologic disorders (eg, diabetes mellitus, diabetic neuropathy, amyloidosis, amyloid polyneuropathy (primary and familial), neuropathies with monoclonal proteins, vasculitic neuropathy, HIV infection, herpes zoster—shingles and postherpetic neuralgia, etc), neuropathy associated with Guillain-Barre syndrome, neuropathy associated with Fabry's disease, entrapment due to anatomic abnormalities, trigeminal and other CNS neuralgias, malignancies, inflammatory conditions or autoimmune disorders (including demyelinating inflammatory disorders, rheumatoid arthritis, systemic lupus erythematosus, Sjogren's syndrome), and cryptogenic causes (idiopathic distal small-fiber neuropathy). Other causes of neuropathic pain include exposure to toxins or drugs (such as arsenic, thallium, alcohol, vincristine, cisplatin and dideoxynucleosides), dietary or absorption abnormalities, immuno-globulinemias, hereditary abnormalities and amputations (including mastectomy). Neuropathic pain may also result from compression of nerve fibers, such as radiculopathies and carpal tunnel syndrome.

Common aetiologies of neurophatic pain which may be treated by compounds contemplated herein include alcohol, diabetes mellitus type 1 and 2, Eosinophilia-myalgia syndrome, Guillain-Barre syndrome, heavy metals (e.g. arsenic, lead, mercury), HIV/AIDS, malignant tumor-related, medications, including antineoplastic drugs, (e.g. amiodarone, aurothioglucose, cisplatinum, dapsone, d4T (stavudine), ddC (zalcitabine,), ddI (didanosine), disulfuram, FK 506, hydralazine, isoniazid, metronidazole, nitrofurantoin, paclitaxel, phenyloin, vincristine) monoclonal gammopathies multiple sclerosis, post-stroke central pain, postherpetic neuralgia, traumatic/compression, carpal tunnel syndrome, radiculopathy (sciatica, etc.) cervical or lumbar radiculopathy, complex regional pain syndrome, spinal cord injury, stump (phantom limb) pain, trigeminal neuralgia, and vasculitis.

Reference to neuropathic pain includes reference to a neuropathic component of nociceptive pain. Thus, subjects to be treated for neuropathic pain in accordance with this embodiment of the present invention are selected on the basis of requiring treatment for the neuropathic pain.

Preferably, the sensibility to pain is reduced by at least 30%, preferably at least 50%, more preferably at least 70% and particularly preferably at least 85%. In a most preferred aspect of the present invention, the sensibility to the neuropathic pain is completely, or substantially completely, removed. To assess the level of reduction of sensibility to pain associated with the analgesia induced by the methods according to the present invention it is possible to conduct tests such as the short form McGill pain questionnaire and/or visual analogue scales for pain intensity and/or verbal rating scales for pain intensity and/or measurement of tactile allodynia using von Frey hairs or similar device. These tests are standard tests within the art and would be well known to the skilled person.

The compounds contemplated herein may also be used in treating the neuropathic pain in any one or more of the following diseases or conditions which cause neuropathic pain or which have a neuropathic pain component: Abdominal Wall Defect, Abdominal Migraine, Achondrogenesis, Achondrogenesis Type IV, Achondrogenesis Type III, Achondroplasia, Achondroplasia Tarda, Achondroplastic Dwarfism, Acquired Immunodeficiency Syndrome (AIDS), Acute Intermittant Porphyria, Acute Porphyrias, Acute Shoulder Neuritis, Acute Toxic Epidermolysis, Adiposa Dolorosa, Adrenal Neoplasm, Adrenomyeloneuropathy, Adult Dermatomyositis, Amyotrophic Lateral Sclerosis, Amyotrophic Lateral Sclerosis-Polyglucosan Bodies, AN, AN 1, AN 2, Anal Rectal Malformations, Anal Stenosis, Arachnitis, Arachnoiditis Ossificans, Arachnoiditis, Arteritis Giant Cell, Arthritis, Arthritis Urethritica, Ascending Paralysis, Astrocytoma Grade I (Benign), Astrocytoma Grade II (Benign), Athetoid Cerebral Palsy, Barrett Esophagus, Barrett Ulcer, Benign Tumors of the Central Nervous System, Bone Tumor-Epidermoid Cyst-Polyposis, Brachial Neuritis, Brachial Neuritis Syndrome, Brachial Plexus Neuritis, Brachial-Plexus-Neuropathy, Brachiocephalic Ischemia, Brain Tumors, Brain Tumors Benign, Brain Tumors Malignant, Brittle Bone Disease, Bullosa Hereditaria, Bullous CIE, Bullous Congenital Ichthyosiform Erythroderma, Bullous Ichthyosis, Bullous Pemphigoid, Burkitt's Lymphoma, Burkitt's Lymphoma African type, Burkitt's Lymphoma Non-african type, Calcaneal Valgus, Calcaneovalgus, Cavernous Lymphangioma, Cavernous Malformations, Central Form Neurofibromatosis, Cervical Spinal Stenosis, Cervical Vertebral Fusion, Charcot's Disease, Charcot-Marie-Tooth, Charcot-Marie-Tooth Disease, Charcot-Marie-Tooth Disease Variant, Charcot-Marie-Tooth-Roussy-Levy Disease, Childhood Dermatomyositis, Chondrodysplasia Punctata, Chondrodystrophia Calcificans Congenita, Chondrodystrophia Fetalis, Chondrodystrophic Myotonia, Chondrodystrophy, Chondrodystrophy with Clubfeet, Chondrodystrophy Epiphyseal, Chondrodystrophy Hyperplastic Form, Chondroectodermal Dysplasias, Chondrogenesis Imperfecta, Chondrohystrophia, Chondroosteodystrophy, Chronic Adhesive Arachnoiditis, Chronic Idiopathic Polyneuritis (CIP), Chronic Inflammatory Demyelinating Polyneuropathy, Chronic Inflammatory Demyelinating Polyradiculoneuropathy, Cicatricial Pemphigoid, Complex Regional Pain Syndrome, Congenital Cervical Synostosis, Congenital Dysmyelinating Neuropathy, Congenital Hypomyelinating Polyneuropathy, Congenital Hypomyelination Neuropathy, Congenital Hypomyelination, Congenital Hypomyelination (Onion Bulb) Polyneuropathy, Congenital Ichthyosiform Erythroderma, Congenital Tethered Cervical Spinal Cord Syndrome, Cranial Arteritis, Crohn's Disease, Cutaneous Porphyrias, Degenerative Lumbar Spinal Stenosis, Demyelinating Disease, Diabetes Mellitus Diabetes Insulin Dependent, Diabetes Mellitus, Diabetes Mellitus Addison's Disease Myxedema, Discoid Lupus, Discoid Lupus Erythematosus, Disseminated Lupus Erythematosus, Disseminated Neurodermatitis, Disseminated Sclerosis, EDS Kyphoscoliotic, EDS Kyphoscoliosis, EDS Mitis Type, EDS Ocular-Scoliotic, Elastosis Dystrophica Syndrome, Encephalofacial Angiomatosis, Encephalotrigeminal Angiomatosis, Enchondromatosis with Multiple Cavernous Hemangiomas, Endemic Polyneuritis, Endometriosis, Eosinophilic Fasciitis, Epidermolysis Bullosa, Epidermolysis Bullosa Acquisita, Epidermolysis Bullosa Hereditaria, Epidermolysis Bullosa Letalias, Epidermolysis Hereditaria Tarda, Epidermolytic Hyperkeratosis, Epidermolytic Hyperkeratosis (Bullous CIE), Familial Lumbar Stenosis, Familial Lymphedema Praecox, Fibromyalgia, Fibromyalgia-Fibromyositis, Fibromyositis, Fibrositis, Fibrous Ankylosis of Multiple Joints, Fibrous Dysplasia, Fragile X syndrome, Generalized Fibromatosis, Guillain-Barre Syndrome, Heinangiomatosis Chondrodystrophica, Hereditary Sensory and Autonomic Neuropathy Type I, Hereditary Sensory and Autonomic Neuropathy Type II, Hereditary Sensory and Autonomic Neuropathy Type III, Hereditary Sensory Motor Neuropathy, Hereditary Sensory Neuropathy type I, Hereditary Sensory Neuropathy Type I, Hereditary Sensory Neuropathy Type II, Hereditary Sensory Neuropathy Type III, Hereditary Sensory Radicular Neuropathy Type I, Hereditary Sensory Radicular Neuropathy Type I, Hereditary Sensory Radicular Neuropathy Type II, Herpes Zoster, Hodgkin Disease, Hodgkin's Disease, Hodgkin's Lymphoma, Hyperplastic Epidermolysis Bullosa, Hypertrophic Interstitial Neuropathy, Hypertrophic Interstitial Neuritis, Hypertrophic Interstitial Radiculoneuropathy, Hypertrophic Neuropathy of Refsum, Idiopathic Brachial Plexus Neuropathy, Idiopathic Cervical Dystonia, Juvenile (Childhood) Dermatomyositis (JDMS), Juvenile Diabetes, Juvenile Rheumatoid Arthritis, Pes Planus, Leg Ulcer, Lumbar Canal Stenosis, Lumbar Spinal Stenosis, Lumbosacral Spinal Stenosis, Lupus, Lupus, Lupus Erythematosus, Lymphangiomas, Migraine (e.g. classic or common in adults), Mononeuritis Multiplex, Mononeuritis Peripheral, Mononeuropathy Peripheral, Monostotic Fibrous Dysplasia, Multiple Cartilaginous Enchondroses, Multiple Cartilaginous Exostoses, Multiple Enchondromatosis, Multiple Myeloma, Multiple Neuritis of the Shoulder Girdle, Multiple Osteochondromatosis, Multiple Peripheral Neuritis, Multiple Sclerosis, Musculoskeletal Pain Syndrome, Neuropathic Amyloidosis, Neuropathic Beriberi, Neuropathy of Brachialpelxus Syndrome, Neuropathy Hereditary Sensory Type I, Neuropathy Hereditary Sensory Type II, Nieman Pick disease Type A (acute neuronopathic form), Nieman Pick disease Type B, Nieman Pick Disease Type C (chronic neuronopathic form), Non-Scarring Epidermolysis Bullosa, Ochronotic Arthritis, Ocular Herpes, Onion-Bulb Neuropathy, Osteogenesis Imperfect, Osteogenesis Imperfecta, Osteogenesis Imperfecta Congenita, Osteogenesis Imperfecta Tarda, Peripheral Neuritis, Peripheral Neuropathy, Perthes Disease, Polyarteritis Nodosa, Polymyalgia Rheumatica, Polymyositis and Dermatomyositis, Polyneuritis Peripheral, Polyneuropathy Peripheral, Polyneuropathy and Polyradiculoneuropathy, Polyostotic Fibrous Dysplasia, Polyostotic Sclerosing Histiocytosis, Postmyelographic Arachnoiditis, Primary Progressive Multiple Sclerosis, Psoriasis, Radial Nerve Palsy, Radicular Neuropathy Sensory, Radicular Neuropathy Sensory Recessive, Reflex Sympathetic Dystrophy Syndrome, Relapsing-Remitting Multiple Sclerosis, Sensory Neuropathy Hereditary Type I, Sensory Neuropathy Hereditary Type II, Sensory Neuropathy Hereditary Type I, Sensory Radicular Neuropathy, Sensory Radicular Neuropathy Recessive, Sickle Cell Anemia, Sickle Cell Disease, Sickle Cell-Hemoglobin C Disease, Sickle Cell-Hemoglobin D Disease, Sickle Cell-Thalassemia Disease, Sickle Cell Trait, Spina Bifida, Spina Bifida Aperta, Spinal Arachnoiditis, Spinal Arteriovenous Malformation, Spinal Ossifying Arachnoiditis, Spinal Stenosis, Stenosis of the Lumbar Vertebral Canal, Still's Disease, Syringomyelia, Systemic Sclerosis, Talipes Calcaneus, Talipes Equinovarus, Talipes Equinus, Talipes Varus, Talipes Valgus, Tandem Spinal Stenosis, Temporal Arteritis/Giant Cell Arteritis, Temporal Arteritis, Tethered Spinal Cord Syndrome, Tethered Cord Malformation Sequence, Tethered Cord Syndrome, Tethered Cervical Spinal Cord Syndrome, Thalamic Pain Syndrome, Thalamic Hyperesthetic Anesthesia, Trigeminal Neuralgia, Variegate Porphyria, Vertebral Ankylosing Hyperostosis amongst others.

Subjects to be treated in accordance with the invention include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention. Particularly contemplated subjects are human subjects.

The compounds of the invention are administered in an amount and in accordance with a regimen effective to achieve the desired outcome (e.g. full or partial inhibition of sodium channel activity). An effective amount is intended to include an amount which, when administered according to the desired dosing regimen, at least partially attains the desired effect. In particular, a treatment effective amount is intended to include an amount which, when administered according to the desired dosing regimen, at least partially attains the desired therapeutic effect, including one or more of: alleviating, eliminating or reducing the frequency one or more symptoms of, preventing or delaying the onset of, inhibiting the progression of, or halting or reversing (partially or altogether) the onset or progression of the particular disorder or condition being treated.

Suitable dosage amounts and dosing regimens can be determined by the attending physician and may depend on the particular condition being treated, the severity of the condition as well as the general age, health and weight of the subject. Suitable dosage amounts may lie in the range of from 1 μg to 1 g of compound, salt, solvate or prodrug, for example, 1 μg-1 mg, 1 mg-10 mg, 10 mg-50 mg, 50 mg-100 mg, 100 mg-500 mg, 500 mg-750 mg or 750 mg-1000 mg. Dosages may be administered once, or multiple times daily, or one or more times weekly, fortnightly or monthly.

The active ingredient may be administered in a single dose or a series of doses. While it is possible for the active ingredient to be administered alone, it is preferable to present it as a composition, preferably as a pharmaceutical composition, with one or more pharmaceutically acceptable adjuvants. Thus, the present invention also relates to the use of a compound of formula (I) or a pharmaceutically acceptable salt or prodrug thereof in the manufacture of a medicament for treating a disease or condition in which undesirable sodium channel activity is involve or implicated.

The formulation of such compositions is well known to those skilled in the art, see for example, *Remington's Pharmaceutical Sciences*, 18$^{th}$ Edition, Mack Publishing, 1990. The composition may contain any suitable additive such as carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches, may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention may also be presented for use in veterinary compositions. These may be prepared by any suitable means known in the art. Examples of such compositions include those adapted for:
(a) oral administration, external application (e.g. drenches including aqueous and non-aqueous solutions or suspensions), tablets, boluses, powders, granules, pellets for admixture with feedstuffs, pastes for application to the tongue;
(b) parenteral administration, e.g. subcutaneous, intramuscular or intravenous injection as a sterile solution or suspension;
(c) topical application e.g. creams, ointments, gels, lotions etc.

The invention will now be described with reference to the following examples which are provided for the purpose of illustrating certain embodiments of the invention and are not intended to limit the generality hereinbefore described.

EXAMPLES

Example 1

Preparation of Compounds 1-8

Compound 1

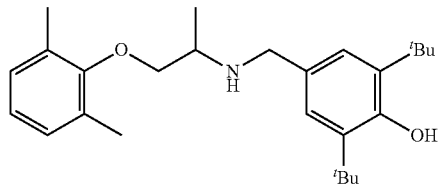

Commercially available mexiletine hydrochloride (2.0 g, 9.24 mmol) was dissolved in dry dichloromethane (25 ml) containing 4A molecular sieves (2 g) and triethylamine (1.28 ml, 9.24 mmol) was added followed by commercially available 3,5-di-t-butyl-4-hydroxybenzaldehyde (3.37 g, 13.86 mmol). The mixture was stirred at room temperature under an atmosphere of nitrogen gas for 18 hours and then refluxed for 5 hours. The reaction mixture was cooled to room temperature and filtered to remove molecular sieves. The solvent was evaporated in a rotary evaporator and the residue was dissolved in methanol (40 ml) and tetrahydrofuran (10 ml) and sodium cyanoborohydride (1.16 g, 18.48 mmol)) was added portion wise and stirring was continued over 18 hours at room temperature under a nitrogen gas atmosphere. The reaction mixture was evaporated to dryness and 100 ml of distilled water was added. This was then extracted with dichloromethane (250 ml) and then dichloromethane layer was washed with a saturated solution of sodium chloride (10 ml). The dichloromethane extract was dried over anhydrous magnesium sulfate powder and the solvent evaporated to give a thick liquid which was chromatographed on a silica gel column and eluted with ethyl acetate/hexane (1:2) to give a light yellow liquid which solidified on storage at 4° C. Mp=61-64° C. Microanalysis for $C_{26}H_{39}O_2N$ C, 78.54; H, 9.89; N, 3.52 (calculated), C, 78.71; H, 9.85; N, 3.59 (obtained).

Compound 2

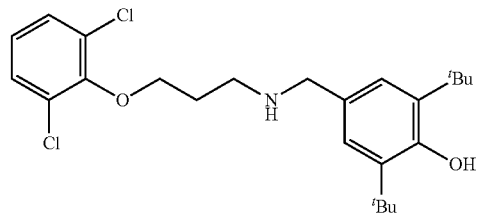

A mixture of 2,6-dichlorophenol (2.0 g, 12 mmol), N-(3-bromopropyl)phthalimide (3.29 g, 12 mmol) and potassium carbonate (1.69 g, 12 mmol) in anhydrous N,N-dimethylformamide (40 ml) was stirred at 100° C. for 4 hours under an atmosphere of nitrogen. The mixture was then poured into 200 ml of distilled water to give a white precipitate, which was filtered and washed with distilled water. The solid was dried in a vacuum desiccator to yield 4.17 g of N-[3(2,6-dichlorophenoxy)propyl] phthalimide which was dissolved in absolute ethanol (75 ml) and hydrazine hydrate (3 ml, 73 mmol) was added and the mixture refluxed for one hour. After cooling to room temperature, the precipitate was filtered off and the filtrate was concentrated. The residue was chromatographed on silica gel column and eluted with dichloromethane/methanol/ammonium hydroxide (9:2:0.2) to yield 3.2 g of 3-(2,6-dichorophenoxy)propylamine.

2,6-Dichlorophenoxy-propylamine (0.5 g, 2.2 mmol) was dissolved in dry dichloromethane and 4A molecular sieves were added followed by 3,5-di-t-butyl-4-hydroxybenzaldehyde (3.3 mmol). The resulting mixture was stirred under an atmosphere of nitrogen at room temperature for 18 hours and then refluxed for 4 hours. The reaction mixture was cooled to room temperature and filtered to remove molecular sieves and the filtrate concentrated in vacuo and then dissolved in methanol (30 ml). Sodium cyanoborohydride (0.3 g, 4.4 mmol)) was added portion wise and stirring was continued over 18 hours at room temperature under a nitrogen gas atmosphere. The reaction mixture was evaporated to dryness in vacuo and 30 ml of distilled water was added. This was then extracted with dichloromethane (150 ml) and then dichloromethane layer was washed with a saturated solution of sodium chloride (10 ml). The dichloromethane extract was dried over anhydrous magnesium sulfate powder and the solvent evaporated to give a thick orange liquid which was chromatographed on a silica gel column and eluted with dichloromethane/methanol (9:1) to yield a yellow thick liquid (0.21 g) which was then dissolved in methanol and cooled in an ice-bath. Ether-HCl was added and the solution was evaporated in vacuo. More ether was added and the washing procedure was repeated three times to yield a hydrochloride salt (MP=84-86° C.). Acc mass calculated for [M+H]$^+$438.1967, obtained 438.1966.

$C_{24}H_{34}Cl_2NO_2$ Calculated HCl salt C 59.65H 7.34 Cl 23.47 N 2.89

Obtained C 60.21H 7.24 Cl 22.41 N 2.89

Tartrate salt formation: The free base (102 mg, 0.23 mmol) was dissolved in ethyl acetate (10 ml), tartaric acid (0.034 g, 0.23 mmol)) in absolute ethanol (2 ml) was added and the solution was stirred on rotary evaporator. The solvent was evaporated in vacuo and to the residue was added ethyl acetate and this washing procedure was repeated three times to yield a tartrate salt.

Compound 3

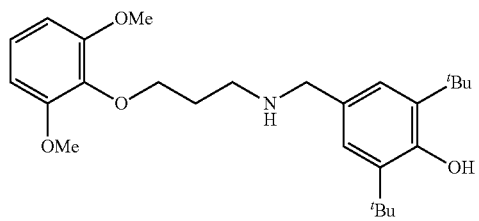

Compound 3 was prepared in an analogous manner to Compound 2 using 2,6-dimethoxyphenol (2 g. 12.9 mmol).

Compound 4

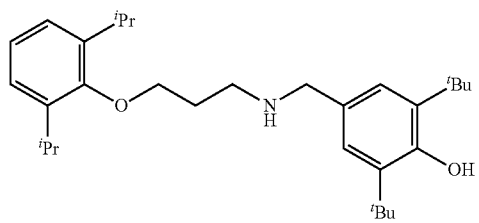

Compound 4 was prepared in an analogous manner to Compound 2 using 2,6-diisopropylphenol (5 g. 28 mmol).

Compound 5

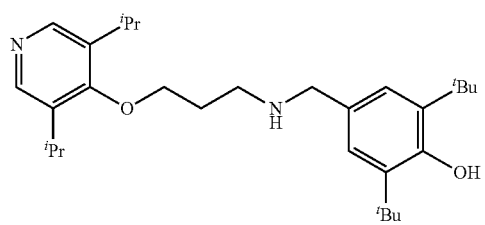

Compound 5 was prepared in an analogous manner to Compound 2 using 3,5-diisopropyl-4-hydroxy-pyridine.

Compound 6

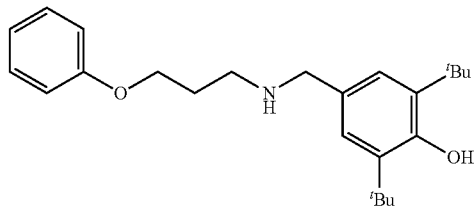

Compound 6 was prepared in an analogous manner to Compound 2 using phenol.

Compound 7

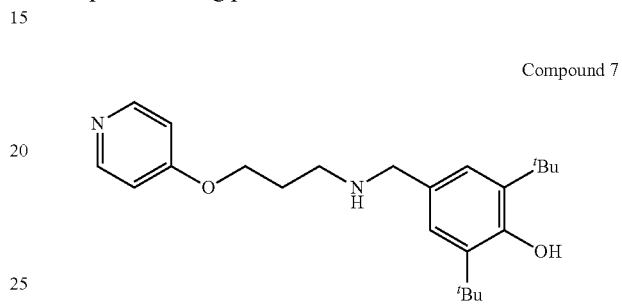

Compound 7 was prepared in an analogous manner to Compound 2 using 4-hydroxy pyridine.

Compound 8

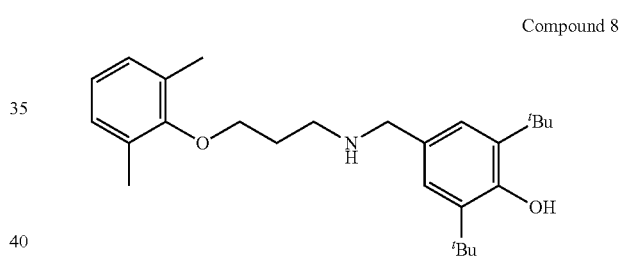

Compound 8 was prepared in an analogous manner to Compound 2 using 2,6-dimethyl phenol (5 g, 4.1 mmol).

Comparative Compound A

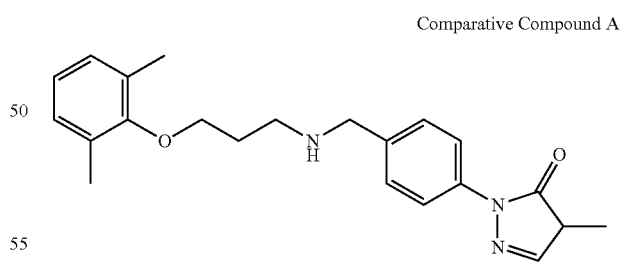

Commercially available 1-hydroxy-benzotriazole (70 mg, 0.5 mmol) in dry dimethylformamide (7 ml) was cooled to 4° C. and then commercially available 4-(3-methyl-5-oxo-2-pyrazolin-1-yl)benzoic acid (100 mg, 0.45 mmol) was added with stirring under an atmosphere of nitrogen. A solution of N,N-dicyclohexylcarbodiimide (103 mg, 0.5 mmol) in dry dimethylformamide (2 ml) was added. After stirring this mixture for one hour at 0° C., mexiletine free base (80 mg, 0.45 mmol) was added in small amounts. The clear solution became progressively cloudy and a precipitate was formed which was stirred for 2 days at room temperature under nitrogen atmosphere. The precipitate was filtered and washed with dichloromethane (1 ml). The filtrate was concentrated in vacuo and the residue was chromatographed on silica gel column and eluted with dichloromethane/methanol (9:1). The residue was triturated with dry hexane to remove dimethylfonnamide and chromatographed on silica gel column and eluted with ethylacetate/hexane (4:1) to give a yellow liquid which solidified in a freezer. Mp=70-71° C. Acc. mass calculated for $[M+H]^+$380.1974, obtained 380.1974.

The compound above (100 mg, 0.26 mmol) was dissolved in dry tetrahydrofuran (7 ml) and heated under an atmosphere of nitrogen gas to reflux. Borane-dimethyl sulfide complex (2 Molar in tetrahydrofuran) was added dropwise (0.24 ml, 0.48 mmol, 1.8 equivalents) via a syringe and the reaction was refluxed overnight. The reaction mixture was cooled to room temperature and concentrated hydrochloric acid in absolute ethanol (1 ml of 30% HCl in 10 ml of absolute ethanol) was added until the solution was acidic (~pH 4). The solution was concentrated and diethyl ether was added. A solid was filtered and washed with ether to yield ~100 mg of a white solid.
Acc. Mass calculated for $[M+H]^+$366.2182, obtained 366.4766.

Example 2

In vitro Assay of Inhibition by Compounds to the Binding of $^3$H-Batrachotoxinin to the Sodium Channel Binding Site 2 in Rat Brain Membranes This method is based on the publication by Catterall et al (1981). Rat brain membranes were prepared from Wistar rats and washed by centrifugation in fresh buffer. Aliquots of membranes were added to tubes and then incubated with $^3$H-batrachotoxinin (5 nM) in the absence or presence of increasing concentrations of the synthesised compounds. After incubation at 37° C. for 60 minutes, membranes were collected by rapid filtration though filters under vacuum and radioactivity in filters were determined by liquid scintillation counting. Non-specific binding of $^3$H-batrachotoxinin to membranes was determined by incubating membranes in a high concentration of veratridine (100 uM) and this was subtracted from all other values to determine specific binding. The concentration of each compound that inhibited specific binding of $^3$H-batrachotoxinin by 50% ($IC_{50}$) was computed by non-linear regression using the EBDA/LIGAND computer software (McPherson, 1985).
In Silico Calculation of Log P Values at pH 1.0 and 7.4

The chemical structures of the synthesised compounds were drawn using the software package PrologD (Compu-Drug Chemistry Ltd, Budapest, Hungary) which also estimates the partition coefficients at a given pH using a published Linear Free Energy Relationship algorithm (Csizmadia, et al, 1997).

The results are depicted in Table 2.1.

TABLE 2.1

| Compound | $IC_{50}$ (µM) | log P (pH 1) | log P (pH 7.4) |
|---|---|---|---|
| 1 | 0.134 | 3.43 | 6.43 |
| 2 | 0.105 | 4.13 | 6.17 |
| 3 | 0.107 | 2.63 | 4.67 |
| 4 | 0.09 | 5.30 | 7.35 |
| 5 | 0.38 | 0.56 | 5.24 |
| 6 | 0.236 | 2.70 | 4.74 |
| 7 | 0.87 | −0.92 | 3.18 |
| 8 | 0.179 | 2.90 | 5.89 |

TABLE 2.1-continued

| Compound | $IC_{50}$ (µM) | log P (pH 1) | log P (pH 7.4) |
|---|---|---|---|
| Comparative A | 11 | −0.1 | 2.48 |
| Mexilitene | 11 | −1.2 | 0.80 |

Example 3

Assessment of Compound 1 as an Analgesic in the Formalin Paw Test of Neuropathic Pain The formalin paw test provides a model of nociception in which a sub-dermal injection of formalin induces a pain that occurs in time-linked phases. Rats typically respond to the injured tissue in a characteristic way that can be quantitated and statistically evaluated. The early phase is thought to be caused by C-fiber activation due to peripheral sensory stimulation, while the late phase is associated with both an inflammatory component and functional changes in the dorsal horn of the spinal cord.

The purpose of this study was to investigate the efficacy of Compound 1 to reduce the pain associated with the rat formalin paw model. In this model, the hind paw dermis of each rat was injected with a solution of formalin or saline and pain behavior was evaluated. Compound 1 and a known sodium channel blocker, Mexiletene were injected intraperitoneally 30 minutes prior to paw injection. Pain behavior was then evaluated at three time points (at 2 to 5, 25 to 30 and 55 to 60 minutes) following paw injection of formalin or saline by counting the number of paw-licking events.

Thirty-four (34) male Sprague-Dawley rats of approximately 200 to 225 grams weight were used in this study. The rats were housed 2 animals per cage and were acclimated for nine (9) days prior to the commencement of experimental procedures. Rats were randomly allocated to treatment groups based on their body weights taken during the acclimation period. Eight (8) animals were allocated to each of four (4) treatment groups.

TABLE 3.1

Study Design

| Group No. | Day | Paw Injection | Treatment | Dose |
|---|---|---|---|---|
| 1 | −2 | saline | vehicle | 5 mL/kg |
|  | 1 | 5% formalin | vehicle | 5 mL/kg |
| 2 | 1 | 5% formalin | Compound 1 | 24 nmol/g |
| 3 | 1 | 5% formalin | Compound 1 | 72 nmol/g |
| 4 | 1 | 5% formalin | Mexiletine HCl | 144 nmol/g |

Dosing

At 30 minutes prior to paw injection of formalin or saline, rats were dosed by intraperitoneal injection of the appropriate drug according to Table 3.1. On Day -2, baseline control rats received a 50 µL injection of saline solution into the dermis of either hind paw at 30 minutes post-dosing with vehicle and immediately prior to behavioral observation. Eight (8) rats received saline injections in the left hind paw. On Day 1, thirty two (32) rats received a 50 µL injection of 5% formalin solution into the dermis of either hind paw at 30 minutes post dosing and immediately prior to behavioral observation.
Behavioral Testing Each rat was placed in an individual plexiglas chamber on an elevated glass surface for the duration of testing. Rats were observed at 2 to 5 minutes (phase 1), 25 to 30 minutes (early phase 2), and again at 55 to 60 minutes (late phase 2) post-paw injection. For each observation interval, the number of paw-licking events were determined.

Figure 2:
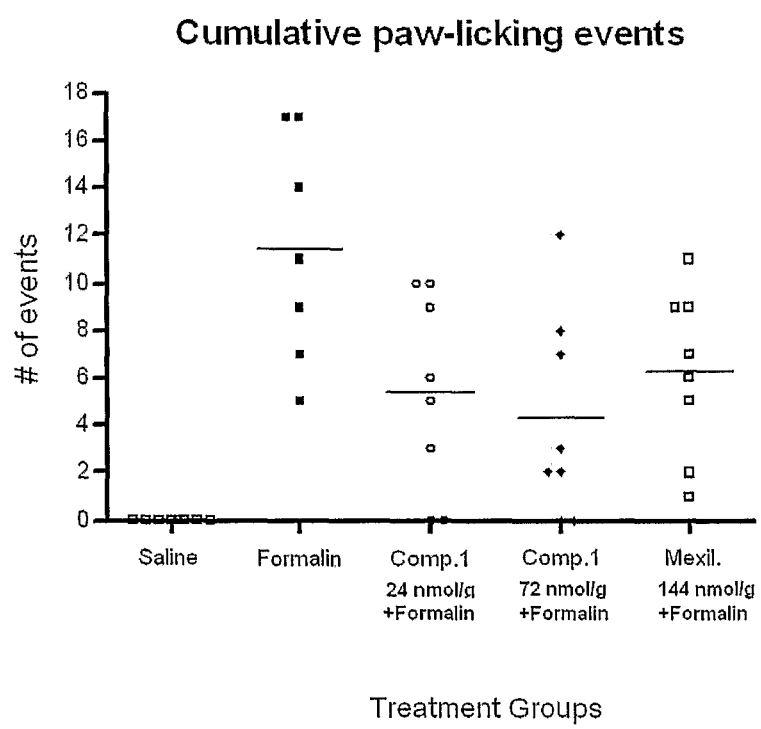
FIG. 2 graphically depicts the individual points and the mean (horizontal line) of the cumulative number of paw-licking events observed in 3×1 minute observation periods in a rat formalin paw model.

The results are depicted in FIGS. 1 and 2.

Example 4

Assessment of Analgesic Actions of Compound 1 in a Rat In vivo Model of Neuropathic Pain The following method is based on the method published by Chaplan et al, 1994. Male Sprague-Dawley rats from one litter were weaned when 19 days old and acclimatized for the next two days in the Animal House where the experiment was to be carried out. From days 21 to 25, rats were tested using a set of Von Frey monofilaments to test the mechanical withdrawal threshold of the hindpaws. The monofilaments were applied in increasing force until the rat withdrew the hind paw being tested. Rats that consistently exhibited a threshold above 10 grams of force were selected for further studies. Rats were anaesthetized with a halothane/oxygen (5:95) gas mixture and a dorsal midline incision was made on the rat's lower back to expose the left lumbar region either side of the hip. Bone was clipped away to expose the L4 and L5 nerves distal to their emergence from the intervertebral foramina. The L5 nerve was then isolated using a glass hook, ligated and cut on the peripheral side of the ligation. The incision was then closed with suture threads and the anaesthetic gas discontinued. The next day rats underwent testing with the graded Von Frey filaments to the hind paws to determine if allodynia was present in the left paw as compared to the right hind paw. Testing was repeated on these rats until they were 28 days old. On that day, rats that displayed allodynia in their left paw only (Rats #17,18,19,20—Table 4.1) were given an intraperitoneal injection of Compound 1 (7 μmmol per 100 g body weight dissolved in 5% ethanol in a volume of 1 ml/100 g). Rats were then tested with graded Von Frey filaments at 45 minutes and 90 minutes after injection in order to determine if allodynia had been blocked. It was found that 45 minutes after an intraperitoneal injection of Compound 1 (70 nmol/g) allodynia had been completely eliminated in 3 of the rats (#17,18,19) while it was reduced in rat # 20 (Table 4.1). At 90 minutes after injection, allodynia had still been eliminated in 2 rats (# 18,19) but allodynia had returned to pre-injection levels in rats # 17,20 (Table 4.1). When the right hindpaw of the 4 rats was tested with the Von Frey filaments, there was no development of any allodynia after cutting the left L5 nerve nor was there any effect of Compound 1 on the response to the filaments at 45 or 90 minutes after injection of Compound 1 showing that Compound 1 did not cause a generalized anaesthesia (Table 4.2).

TABLE 4.1

Left Hind Paw - nerve cut on day 3 - grams of force needed to withdraw left limb

| Rat | Pre-op 1 | Pre-op 2 | Baseline | 45 min post Compound 1 | 90 min post Compound 1 |
|---|---|---|---|---|---|
| #17 | 17.8 g | 17.8 g | 10.46 g | 17.8 g | 10.9 g |
| #18 | 17.8 g | 17.8 g | 7.95 g | 17.8 g | 17.8 g |
| #19 | 17.8 g | 17.8 g | 3.86 g | 17.8 g | 17.8 g |
| #20 | 17.8 g | 17.8 g | 5.61 g | 11.44 g | 3.7 g |

TABLE 4.2

Right Hind Paw - nerve intact - grams of force needed to withdraw right limb

| Rat | Pre-op 1 | Pre-op 2 | Baseline | 45 min post Compound 1 | 90 min post Compound 1 |
|---|---|---|---|---|---|
| #17 | 17.8 g | 17.8 g | 17.8 g | 17.8 g | 17.8 g |
| #18 | 17.8 g | 17.8 g | 17.8 g | 17.8 g | 17.8 g |
| #19 | 17.8 g | 17.8 g | 17.8 g | 17.8 g | 17.8 g |
| #20 | 17.8 g | 17.8 g | 17.8 g | 17.8 g | 17.8 g |

Example 5

Recovery Time in a Reversible Spinal Cord Injury Model

Male Hooded Wistar rats were anesthetized (2% isoflurane/98% oxygen), and laminectomy performed at spinal level T12. An inflatable balloon catheter was inserted rostral, underneath the vertebra, to T10 and inflated for 5 minutes, causing reversible paraplegia (Feldblum, et al., 2000). This model demonstrates a slow, graded return of hindlimb motor function over 15 days. Rats had almost complete functional recovery by 15 d. Compound 1 (15 nmol/g and 60 nmol/g), mexiletine (60 nmol/g) and vehicle (5 ml/kg) were administered i.p, at 3 h after the injury and twice daily thereafter, until killed. Behavioural tests were conducted every 3 days. At 15 d post-injury, rats were anesthetized and transcardially perfused, to fix the spinal cords. Sections were cut and processed to examine the size of the cyst and modulatory effects of treatments or control on lesion formation.

Figure 3:
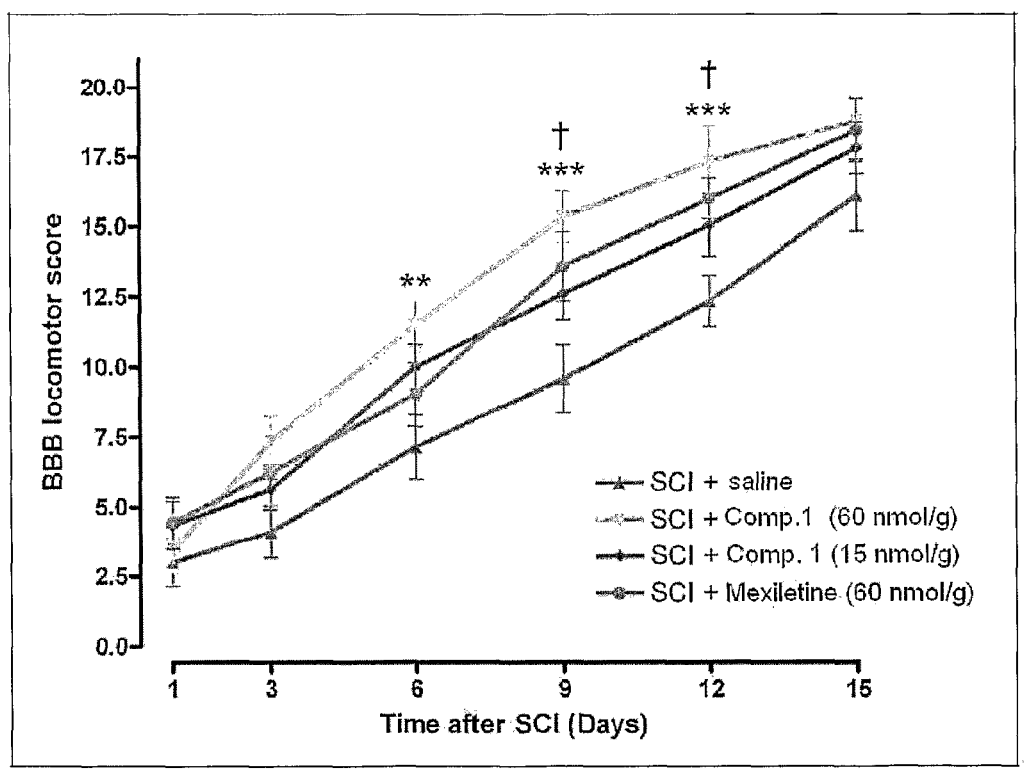
FIG. 3 graphically depicts the effects of mexiletine and Compound 1 on functional recovery following SCI as measured by BBB open-field locomotor.

BBB scale: Effects of Compound 1 and mexiletine treatment on the time course of functional recovery, following SCI, assessed with the BBB open-field locomotor score. Both Compound 1 and mexiletine significantly increased the rate of recovery following SCI, compared to the vehicle treated controls. Each rat acted as its own control, and results after SCI compared with pre-injury scores (0 h after SCI). The results are presented in FIG. 3. Data are mean±SEM. ANOVA followed by Bonferroni post-test: $[F(24,273)=10.57, P<0.0001]$, *$P<0.05$, $P<0.01$, *$P<0.001$ Compound 1 (60 nmol/g) versus the SCI+saline controls at the same time; †$P<0.05$ Compound 1 (15 nmol/g) or mexiletine (60 nmol/g) versus SCI+saline controls at the same time. Mexiletine (60 nmol/g) and Compound 1 (15 nmol/g) showed no significant difference from each other at any time. n=6-11 rats in each group.

Figure 4:
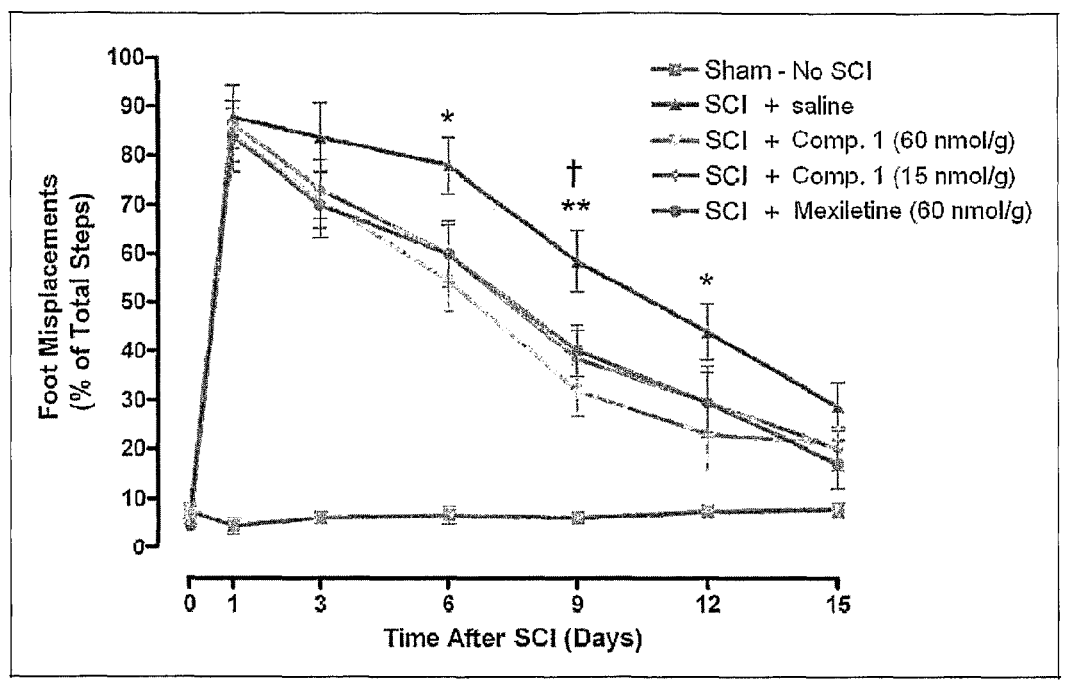
FIG. 4 graphically depicts the effects of mexiletine and Compound 1 on foot misplacement in the horizontal ladder test following SCI.

Ladder test: In the horizontal ladder test, rats are placed onto a beam which is randomly missing rungs, this prevents rats from adapting and compensating for any deficits following SCI. In the ladder test, SCI+saline treated rats showed increased foot misplacements which decreased over the 15 day test period, but remained significantly different from pre-SCI. The results are depicted in FIG. 4. Treatment with Compound 1 or mexiletine decreased the number of hindlimb foot misplacements when compared to SCI+saline controls at the same time. Data is expressed as the percentage of foot misplacements made of the total number of steps taken, using a combined score for both hindlimbs. (If rats were found to have significant differences between the hind paws they were excluded from the study). Each rat acted as its own control, and results compared with pre-injury scores (0 h after SCI). ANOVA followed by Bonferroni post-test: $[F(24,273)= 5.94, P<0.0001]$, *$P<0.05$, **$P<0.01$ Compound 1 (60 nmol/g) versus the SCI+saline controls at the same time;

†P<0.05 Compound 1 (15 nmol/g) and mexiletine (60 nmol/g) versus SCI+saline controls at the same time. Mexiletine (60 nmol/g) showed no significant difference from Compound 1(15 or 60 nmol/g) at any time. Data are mean±SEM. n=6-11 rats in each group.

Figure 5:
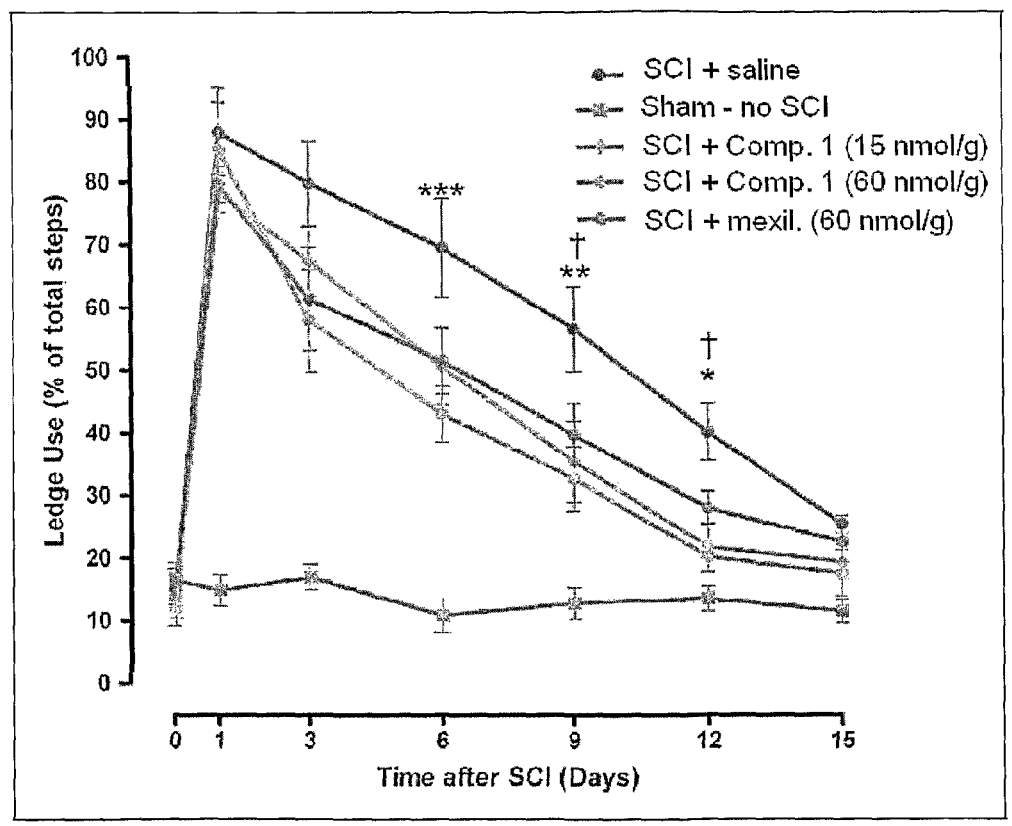
FIG. 5 graphically depicts the effects of mexiletine and Compound 1 on ledge use following SCI.

Ledged beam: Effects of Compound 1 and mexiletine, and SCI+saline controls on recovery of function following spinal cord compression injury as assessed by the number of steps using the support ledge on the ledged beam task. The results are depicted in FIG. 5. Sham-SCI rats walked the length of the ledged beam with approximately 10% of steps made on the supporting ledge. Saline-treated control rats relied on the support ledge significantly more than shams during the course of recovery. Use of the support ledge was significantly reduced in rats treated with either Compound 1 or mexiletine. Data is expressed as ledge use/errors made as a percentage of total steps taken with both hindlimbs after SCI. Each rat acted as its own control, and results compared with pre-injury scores (0 h after SCI). ANOVA followed by Bonferroni post-test: [F(24,273)=5.12, P<0.0001], *P<0.05, P<0.01, *P<0.001 Compound 1 (60 nmol/g) versus the SCI+saline controls at the same time; †P<0.05 Compound 1 (15 nmol/g) versus SCI+saline controls at the same time. Mexiletine (60 nmol/g) showed no significant difference from SCI+saline at any time. Data are mean±SEM. n=6-11 rats in each group.

Figure 6:
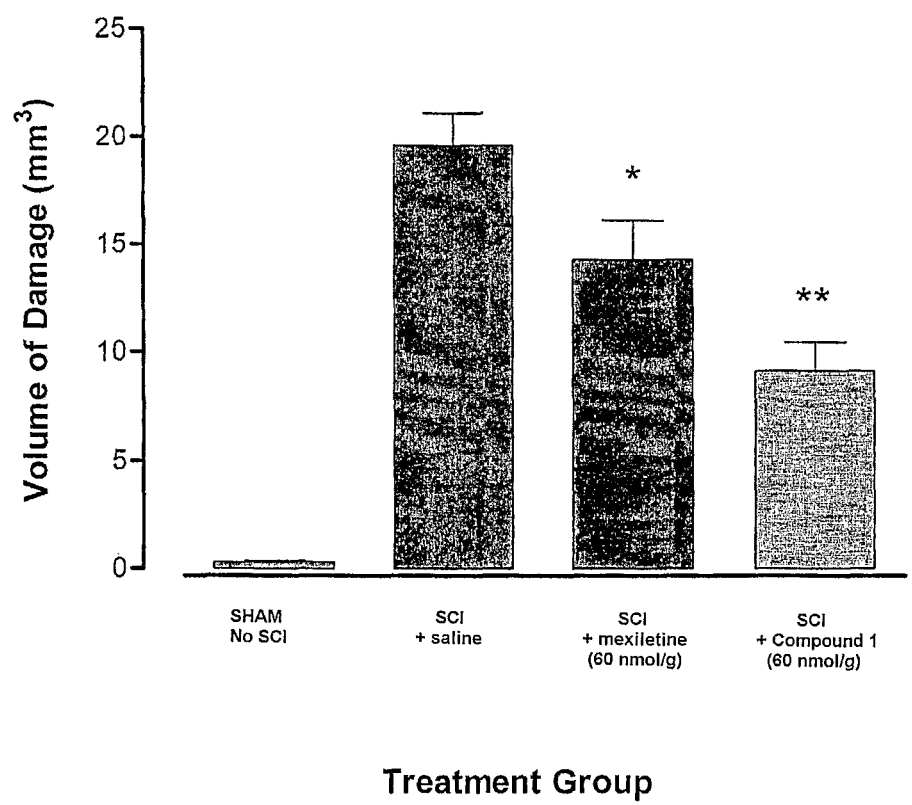
FIG. 6 graphically depicts the effects of mexiletine and Compound 1 on volume of damage (as a whole of both white and gray matter) following SCI.

Volume of damage: Effects of treatment were measured first from H & E stained sections. The results are presented in FIG. 6. Sham-injury rats showed only minor damage associated with laminectomy and balloon insertion. SCI+saline vehicle controls showed increased damage. Mexiletine and Compound 1 at an equivalent mole dose showed reduced damage compared to SCI+saline. Data are mean±SEM of measurements from n=4 rats per treatment group. Secondly, the sparing of spinal cord tissue by Compound 1 and mexiletine treatment was assessed by more detailed histological staining techniques. Compound 1 and Mexiletine treatment showed better preservation of the cytoarchitecture in both H & E and luxol-fast blue (a myelin stain) stained coronal sections after SCI than saline treatment (Table 5.1). When this was examined in more detail in rostro-caudal serial sections stained both for myelin and grey matter and also by counting neuronal cell bodies (Table 5.2), this showed that treatment with Compound 1 and Mexiletine reduced loss of both white matter and gray matter. Again, Compound 1 was more effective than Mexiletine.

TABLE 5.1

Thin tissue sections (16 um) were taken at the epicentre of the spinal cord after spinal cord injury (SCI), stained with Haematoxylin and Eosin (H & E) as well as Luxol Fast blue and cresyl violet staining in order to quantitate the percentage of white matter and gray matter that was spared from destruction. Treatment with Compound 1 and Mexiletine significantly increased the percentage of tissue that survived SCI.

| | Dose | % MEAN | ±SE |
|---|---|---|---|
| TOTAL TISSUE | | | |
| SCI + saline | | 53.6 | 8.04 |
| SCI + Mexiletine | 60 nmol/g | 70.5* | 5.89 |
| SCI + Compound 1 | 60 nmol/g | 83.9* | 5.71 |
| SCI + Compound 1 | 15 nmol/g | 74.3* | 6.25 |
| WHITE MATTER | | | |
| SCI + saline | | 45.5 | 7.86 |
| SCI + Mexiletine | 60 nmol/g | 66.3* | 6.43 |
| SCI + Compound 1 | 60 nmol/g | 81.1* | 5.18 |
| SCI + Compound 1 | 15 nmol/g | 63.6* | 6.79 |
| GRAY MATTER | | | |
| SCI + saline | | 62.5 | 8.75 |
| SCI + Mexiletine | 60 nmol/g | 77.9* | 5 |
| SCI + Compound 1 | 60 nmol/g | 88.9* | 5.18 |
| SCI + Compound 1 | 15 nmol/g | 80* | 4.64 |

*$P < 0.05$ compared to SCI + saline treatment

TABLE 5.2

Neuronal cell bodies were counted in thin tissue sections of 16 μm taken at 0.5 mm intervals rostral (−) and caudal (+) to the lesion epicentre (0.0) after spinal cord injury (SCI) using NeuN immunostaining.

| | | | Dist from epicentre | | | | | | | | | | | | | | | | | | |
|---|---|---|---|---|---|---|---|---|---|---|---|---|---|---|---|---|---|---|---|---|---|
| No. of motor neurons | Per sq mm | | −2.5 mm | | −2 mm | | −1.5 mm | | −1 mm | | −0.5 mm | | 0.0 mm | | +0.5 mm | | +1 mm | | +1.5 mm | | +2 mm | | +2.5 mm |
| | Mean | SE | Mean | SE | Mean | SE | Mean | SE | Mean | SE | Mean | SE | Mean | SE | Mean | SE | Mean | SE | Mean | SE | Mean | SE |
| Sham, No SCI | 29 | 2 | 32 | 3 | 31 | 2 | 31 | 3 | 32 | 2 | 30 | 3 | 32 | 3 | 33 | 3 | 30 | 2 | 33 | 2 | 31 | 2 |
| SCI + saline | 32 | 1 | 27 | 2 | 22 | 1 | 9 | 1 | 4 | 1 | 4 | 2 | 3 | 2 | 8 | 2 | 15 | 2 | 31 | 2 | 31 | 2 |
| SCI + mex. 60 nmol/g | 31 | 1 | 33 | 1 | 26 | 1 | 17* | 2 | 11* | 2 | 7* | 3 | 10* | 2 | 17* | 2 | 24* | 1 | 30 | 1 | 27 | 2 |
| SCI + Comp 1 60 nmol/g | 30 | 2 | 30 | 3 | 26 | 2 | 23* | 2 | 17* | 2 | 15* | 3 | 16* | 2 | 22* | 2 | 29* | 2 | 28 | 2 | 30 | 2 |
| SCI + Comp 1 15 nmol/g | 27 | 1 | 29 | 2 | 26 | 2 | 18* | 2 | 11* | 2 | 9* | 1 | 10* | 2 | 14* | 2 | 25* | 2 | 28 | 1 | 29 | 1 |

*$P < 0.05$ compared to SCI + saline

Figure 7:
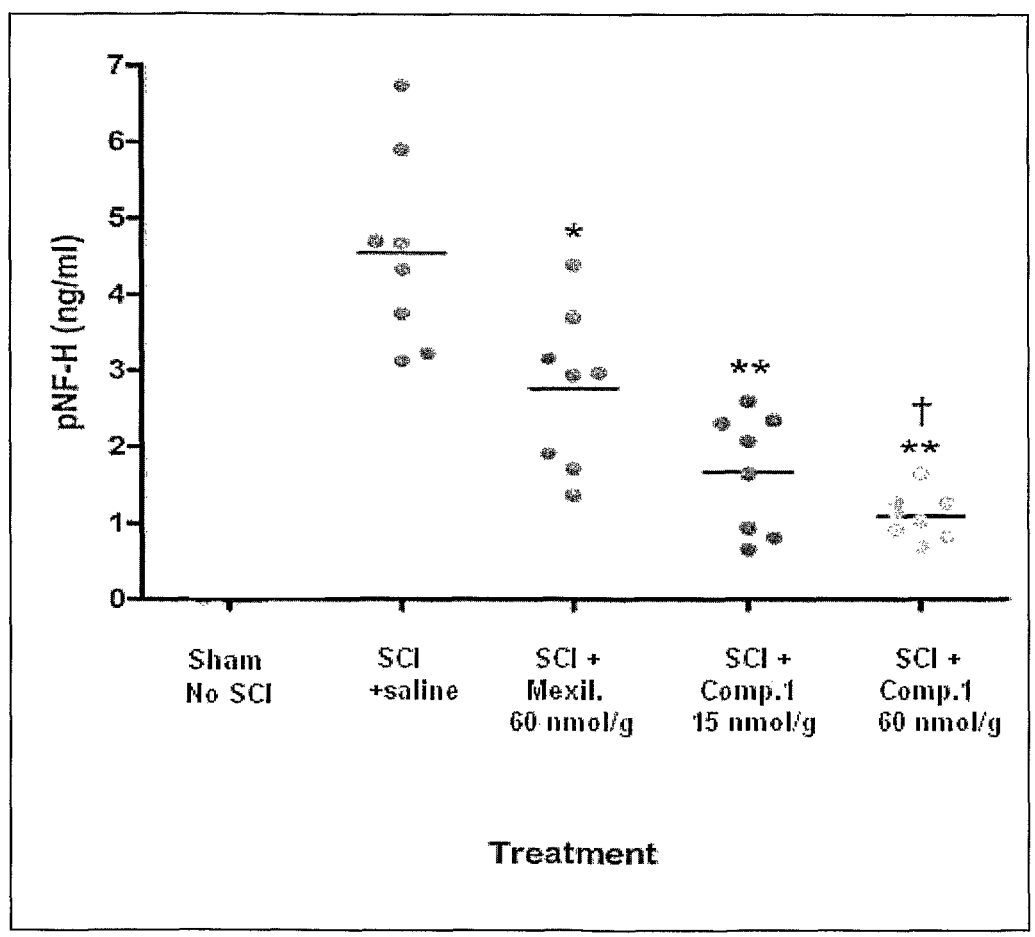
FIG. 7 graphically depicts the effects of mexiletine and Compound 1 on plasma pNF—H levels (a marker of axonal damage) in SCI.

Phosphorylated Neurofilament H (pNF—H) is a biomarker of axonal injury and degeneration. It has shown to be readily detectable in the sera of rodents with experimental SCI (Shaw et al, 2005). Previous findings have shown that plasma pNF—H levels and behavioural outcomes can be correlated following EAE. Plasma pNF—H levels were determined in healthy controls (SHAM) and SCI injured animals (saline, mexiletine and Compound 1 treated rats). The results are depicted in FIG. 7.

BIBLIOGRAPHY

Agrawal S. K., Fehlings M. G., The effect of the sodium channel blocker QX-314 on recovery after acute spinal cord injury. *J. Neurotrauma* 14:81-88, 1997.

Baron R., Peripheral neuropathic pain: from mechanisms to symptoms. *Clin. J. Pain* 16 (suppl2):S12-S20, 2000.

Bechtold et al., Axonal protection mediated by flecainide therapy in experimental inflammatory demyelinating disease. *Ann Neurol* 55:607-616, 2004.

Bechtold et al., Axonal protection in experimental autoimmune neuritis by the sodium channel blocking agent flecainide. *Brain* 128:18-28, 2005.

Butera J. A., Current and emerging targets to treat neuropathic pain, *J. Med. Chem.* 50:2543-2546, 2007

Catterall et al, Binding of batrachotoxinin A 20-α-benzoate to a receptor site associated with sodium channels in synaptic nerve ending particles. *The Journal of Biological Chemistry* 256: 8922-8927, 1981

Chao T. I., Alzheimer C., Effects of phenyloin on the persistent $Na^+$ current of mammalian CNS neurones. *NeuroReport* 6:1778-1780, 1995.

Chaplan, et al, Quantitative assessment of allodynia in the rat paw. *Journal of Neuroscience Methods*, Vol. 53: pages 55-63, 1994.

Craner et al., Colocalization of sodium channel $Na_v1.6$ and the sodium-calcium exchanger at sites of axonal injury in the spinal cord in EAE. *Brain* 127 (Pt 2):294-303, 2004.

Craner et al., Sodium channels contribute to microglia/macrophage activation and function in EAE and MS. *GLIA* 49:220-229, 2005.

Csizmadia, et al Prediction of distribution coefficient from structure. 1. Estimation Method. *Journal of Pharmaceutical Sciences* 86: 865-871, 1997).

De Andres and Garcia-Ribas, Neuropathic Pain Treatment: The Challenge. *Pain Practice*, 3:1-7, 2003

Devor et al, $Na^+$ channel immunolocalization in peripheral mammalian axons and changes following nerve injury and neuroma formation. *J. Neurosci.*, 132, 1976-1992, 1993.

Feldblum,. et al, Efficacy of a new neuroprotective agent, gacyclidine, in a model of rat spinal cord injury. *Journal of Neurotrauma*, 17:1079-1093, 2000

Fern et al., Pharmacological protection of CNS white matter during anoxia: actions of phenyloin, carbamazepine and diazepam. *J. Pharmacol. Exp. Ther.* 266:1549-1555, 1993.

Haim et al., Sodium channel blockade with phenyloin protects spinal cord axons, enhances axonal conduction, and improves functional motor recovery after contusion SCI, *Experimental Neurology* 188:365-377, 2004.

Haim et al., Altered sodium channel expression in second-order spinal sensory neurons contributes to pain after peripheral nerve injury, *J. Neurosci.* 24:4832-4839, 2004 b Imaizumi et al., Anoxic injury in the rat spinal cord: pharmacological evidence for multiple steps in $Ca^{2+}$-dependent injury of the dorsal columns. *J. Neurotrauma* 14:299-311, 1997.

Kapoor et al., Blockers of sodium and calcium entry protect axons from nitric oxide-mediated degeneration. *Ann Neurol* 53:174-180, 2003.

Kobrine et al., Effect of intravenous lidocaine on experimental spinal cord injury. *J. Neurosurg.* 60:595-601, 1984.

Kyle & Ilyin, Sodium Channel Blockers, *J. Med. Chem.* 50:2583-2588, 2007

Lo et al., Neuroprotection of axons with phenyloin in experimental allergic encephalomyelitis. *NeuroReport* 13:1909-1912, 2002.

Lo et al., Phenyloin protects spinal cord axons and preserves axonal conduction and neurological function in a model of neuroinflammation in vivo. *J Neurophysiol* 90:3566-3571, 2003.

McPherson, Analysis of radioligand binding experiments: A collection of computer programs for the IBM PC. *Journal of Pharmacological Methods* 14: 213-228, 1985.

Mersky and Bogduk, *Classifications of Chronic Pain, 2nd edit Seattle IASP Press:* 394, 1994.

Rosenberg et al., Effects of the sodium channel blocker tetrodotoxin on acute white matter pathology after experimental contusive spinal cord injury. *J Neurosci* 19:6122-6133, 1999.

Schwartz G., Fehlings M. G., Evaluation of the neuroprotective effects of sodium channel blockers after spinal cord injury: improved behavioral and neuroanatomical recovery with riluzole. *J. Neurosurg.* 94:245-256, 2001.

Segal M. M., Douglas A. F., Late sodium channel openings underlying epileptiform activity are preferentially diminished by the anticonvulsant phenyloin. *J. Neurophysiol.* 77:3021-3034, 1997.

Shaw et al, Hyperphosphorylated neurofilament NF—H is a serum biomarker of axonal injury, *BioChem Biophys Res Commun,* 336(4):1268-77, 2005.

Stys et al., Tertiary and quaternary local anesthetics protect CNS white matter from anoxic injury at concentrations that do not block excitability. *J Neurophysiol* 67:236-240, 1992a.

Stys et al., Ionic mechanisms of anoxic injury in mammalian CNS white matter: role of $Na^+$ channels and $Na^+$—$Ca^{2+}$ exchanger. *J Neurosci* 12:430-439, 1992b.

Stys et al., Noninactivating, tetrodotoxin-sensitive $Na^+$ conductance in rat optic nerve axons. *Proc Natl Acad Sci USA* 90:6976-6980, 1993.

Tanelian, et al, Sodium channel blocking agents: Their use in neuropathic pain conditions. *Pain Forum,* 4(22), 75-80, 1995

Teng Y. D., Wrathall J. R., Local blockade of sodium channels by tetrodotoxin ameliorates tissue loss and long-term functional deficits resulting from experimental spinal cord injury. *J. Neurosci.* 17:4359-4366, 1997.

Woolf and Mannion, Neuropathic pain: aetiology, symptoms, mechanisms and management. *Lancet* 353:1959-64, 1999.

The invention claimed is:

1. A compound of Formula (I):

A-O-$L_1$-NR-$L_2$-B wherein

A is an optionally substituted cyclopentadi-2,4-en-1-yl or phenyl group, an optionally substituted 5-6-membered monocyclic heteroaryl group, an optionally substituted napthyl group or an optionally substituted 9-10-membered bicyclic heteroaryl group;

$L_1$ is a $C_{1-4}$ alkylene group, a $C_{2-4}$ alkenylene group or a $C_2$-$C_4$ alkynylene group, each of which may be optionally substituted by $C_{1-6}$ alkyl;

$L_2$ is a $C_{1-4}$ alkylene group, a $C_{2-4}$ alkenylene group or a $C_2$-$C_4$ alkynylene group, each of which may be optionally substituted by $C_{1-6}$ alkyl, or $L_2$ is a $CO_2$ group;

R is hydrogen or a $C_{1-6}$ alkyl group; and

B is a group of formula (a) below:

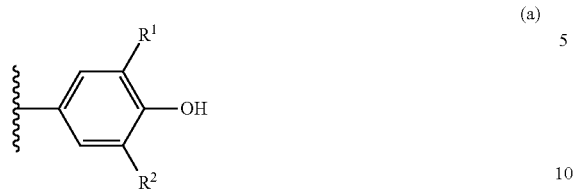

(a)

wherein $R^1$ and $R^2$ are independently selected from hydrogen, $C_{1-6}$ alkyl and $C_{3-6}$ cycloalkyl provided that at least one of $R^1$ and $R^2$ is $C_{1-6}$ alkyl or $C_{3-6}$ cycloalkyl;
or a pharmaceutically acceptable salt or solvate thereof.

2. The compound of claim 1 wherein $R^1$ and $R^2$ are independently $C_{1-6}$ alkyl or $C_{3-6}$ cycloalkyl.

3. The compound of claim 1 wherein $C_{1-6}$ alkyl is t-butyl.

4. The compound of any one of claims 1 and 3 wherein A is substituted or unsubstituted phenyl or substituted or unsubstituted 6-membered heteroaryl.

5. The compound of any one of claims 1 and 3 wherein $L_1$ and $L_2$ are independently selected from substituted or unsubstituted $C_{1-4}$ alkylene.

6. A composition comprising a compound as claimed in any one of claims 1 and 3 together with a pharmaceutically acceptable additive.

7. The compound of claim 5 wherein $L_1$ and $L_2$ are unsubstituted.

8. The compound of claim 7 wherein $L_1$ is unsubstituted ethylene or propylene and $L_2$ is unsubstituted methylene.

* * * * *

UNITED STATES PATENT AND TRADEMARK OFFICE
CERTIFICATE OF CORRECTION

PATENT NO.         : 8,716,528 B2                                    Page 1 of 1
APPLICATION NO.  : 12/741124
DATED              : May 6, 2014
INVENTOR(S)       : Bevyn Jarrott It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this

Twenty-ninth Day of September, 2015

Michelle K. Lee
*Director of the United States Patent and Trademark Office*